(12) United States Patent
Hattori et al.

(10) Patent No.: US 6,384,072 B1
(45) Date of Patent: May 7, 2002

(54) BENZOCYCLOHEPTENE DERIVATIVES

(75) Inventors: Kouji Hattori; Akira Tanaka, both of Takarazuka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/529,412

(22) PCT Filed: Oct. 26, 1998

(86) PCT No.: PCT/JP98/04848

§ 371 Date: Apr. 27, 2000

§ 102(e) Date: Apr. 27, 2000

(87) PCT Pub. No.: WO99/24397

PCT Pub. Date: May 20, 1999

(30) Foreign Application Priority Data

Nov. 10, 1997 (AU) ............................................. PP0291

(51) Int. Cl.$^7$ .................. A61K 31/335; C07D 313/06; C07D 303/02; C07C 205/04
(52) U.S. Cl. ........................ 514/450; 549/355; 549/545; 560/12
(58) Field of Search .......................... 514/450; 549/355, 549/545; 560/21

(56) References Cited

U.S. PATENT DOCUMENTS

| 5,763,489 A | 6/1998 | Taniguchi et al. |
| 5,863,918 A | 1/1999 | Taniguchi et al. |
| 5,972,965 A | 10/1999 | Taniguchi et al. |
| 6,025,375 A | 2/2000 | Taniguchi et al. |

FOREIGN PATENT DOCUMENTS

| EP | 0 542 203 A | * | 5/1993 |
| WO | 95 24393 A | * | 9/1995 |

* cited by examiner

*Primary Examiner*—T. A. Solola
(74) *Attorney, Agent, or Firm*—Oblon, Spivak, McClelland, Maier & Neustadt, P.C.

(57) ABSTRACT

This invention relates to benzocycloheptene derivatives having novel structure. More particularly, it relates to new benzocycloheptene derivatives and pharmaceutically acceptable salts thereof, their production processes, a pharmaceutical composition containing the same and a use thereof for the manufacture of medicaments.

8 Claims, No Drawings

BENZOCYCLOHEPTENE DERIVATIVES

This appln. is a 371 of PCT/J98/04848102 filed Oct. 26, 1998.

FIELD OF THE INVENTION

This invention relates to new benzocycloheptene derivatives and salts thereof which are useful as a medicament.

RELATED ART

Prostaglandins are known as autacoids that show a various kind of biological effects. Specifically, prostaglandin $I_2$ (hereinafter, referred as $PGI_2$) is known to have inhibitory activity on platelet aggregation, vasodilating activity, antihypertensive activity or the like. Therefore, $PGI_2$ agonists are expected to show the above activities which are useful as a medicament for therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension, dermatosis or the like.

So far, some 4,5-diaryloxazole compounds having pharmacological activities as $PGI_2$ agonists have been known, for example, in WO 95/17393, WO 95/24393, WO 97/03973, EP 0 542 203 and U.S. Pat. No. 5,362,879.

DISCLOSURE OF THE INVENTION

This invention relates to benzocycloheptene derivatives having novel structure. More particularly, it relates to new benzocycloheptene derivatives and pharmaceutically acceptable salts thereof, their production processes, a pharmaceutical composition containing the same and a use thereof for the manufacture of medicaments.

Accordingly, an object of this invention is to provide new and useful benzocycloheptene derivatives and pharmaceutically acceptable salts thereof.

Another object of this invention is to provide processes for the production of the benzocycloheptene derivatives and salts thereof.

A further object of this invention is to provide a pharmaceutical composition containing, as an active ingredient, said benzocycloheptene derivatives or pharmaceutically acceptable salts thereof.

Another object of this invention is to provide a use of the benzocycloheptene derivatives and pharmaceutically acceptable salts thereof as a prostaglandin $I_2$ agonist.

Still further object of this invention is to provide a use of the benzocycloheptene derivatives and pharmaceutically acceptable salts thereof for the manufacture of medicament for therapeutic and/or prophylactic treatment of arterial obstruction, cerebrovascular disease, hepatic cirrhosis, arteriosclerosis, ischemic heart disease, restenosis or ischemic complications after coronary angioplasty, hypertension, dermatosis or the like.

The benzocycloheptene derivatives of this invention can be represented by the following formula (I):

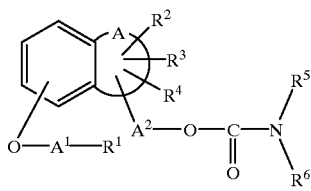

wherein $R^1$ is a carboxy group or a protected carboxy group, $R^2$ and $R^3$ are each a hydrogen atom, a hydroxy group or a protected hydroxy group, or may be combined together to form an oxo group or a lower alkylene group, $R^4$ is a hydrogen atom, a hydroxy group or a protected hydroxy group, $R^5$ and $R^6$ are each an optionally substituted aryl group, $A^1$ and $A^2$ are each a lower alkylene group, and A and two adjacent carbon atoms of the benzene ring to be bonded with A form a seven-membered ring optionally containing an oxygen atom and optionally substituted with an epoxy group.

Suitable pharmaceutically acceptable salts of the object compounds (I) and compounds (II) and (IV) are conventional non-toxic salts, specifically metal salts such as alkaline metal salts (e.g., sodium or potassium salt) and alkaline earth metal salts (e.g., calcium or magnesium salt), ammonium salts, organic base salts (e.g., trimethylamine, triethylamine, pyridine, picoline, dicyclohexylamine or N,N'-dibenzylethylenediamine salt), organic acid salts (e.g., acetate, maleate, tartrate, methanesulfonate, benzenesulfonate, formate, toluenesulfonate or trifluoroacetate), inorganic acid salts (e.g., hydrochloride, hydrobromide, sulfate or phosphate), salts with an amino acid (e.g., arginine salt, aspartate or glutamate) and the like.

It is to be noted that the object compounds (I) may include one or more stereoisomers due to asymmetric carbon atoms and double bond, and that all of such isomers and a mixture thereof are included within the scope of the present invention.

It is also to be noted that the solvating form of the compounds (I) (e.g., hydrate, etc.) and any crystalline form of the compounds (I) are included within the scope of the present invention.

Also included in the scope of invention are radiolabelled derivatives of the compounds (I) which are suitable for biological studies.

The new benzocycloheptene derivatives (I) and salts thereof can be prepared by processes which are illustrated in following scheme.

Process 1

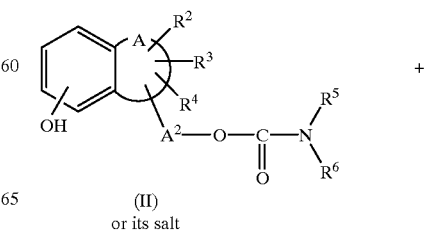

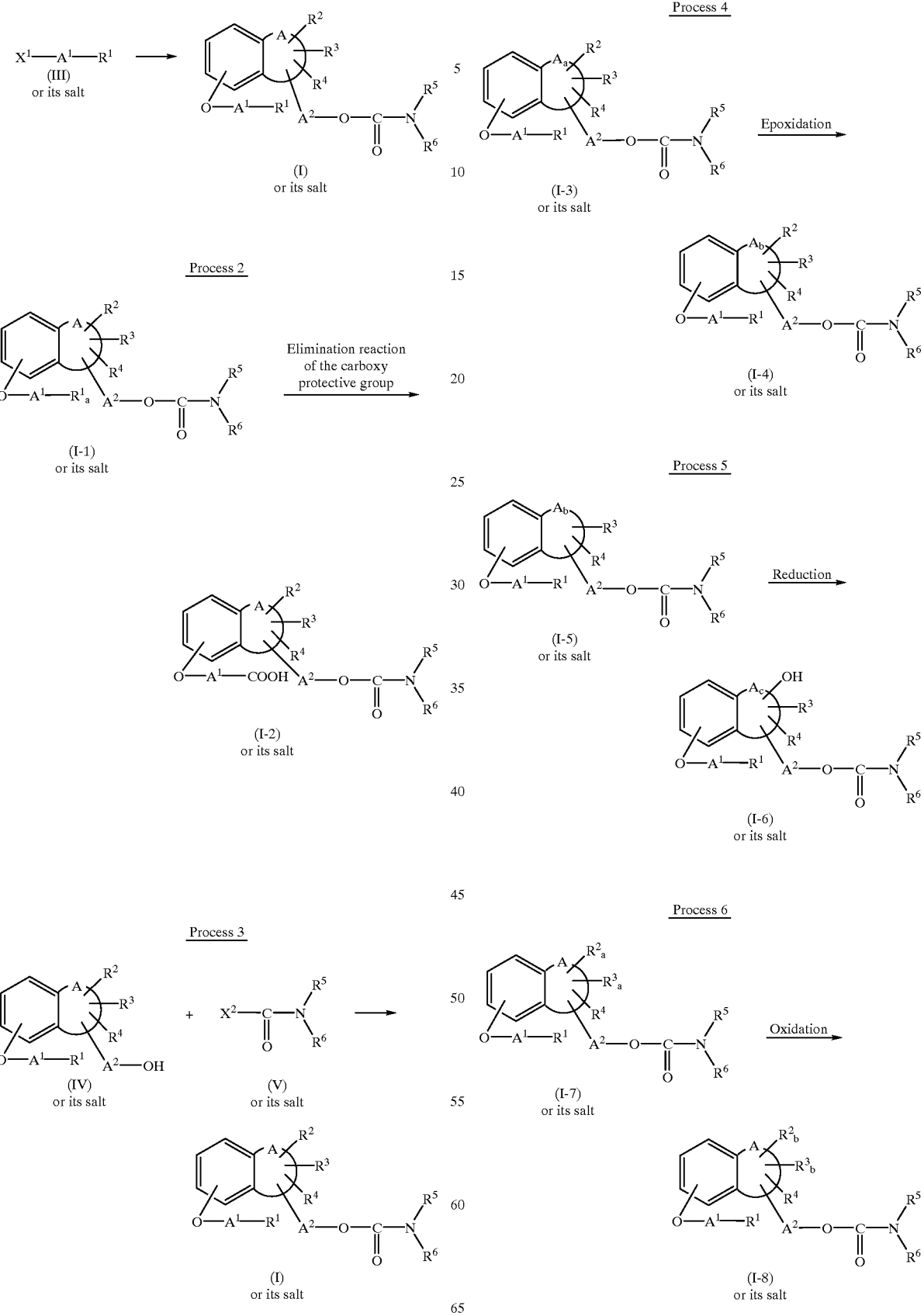

Process 7

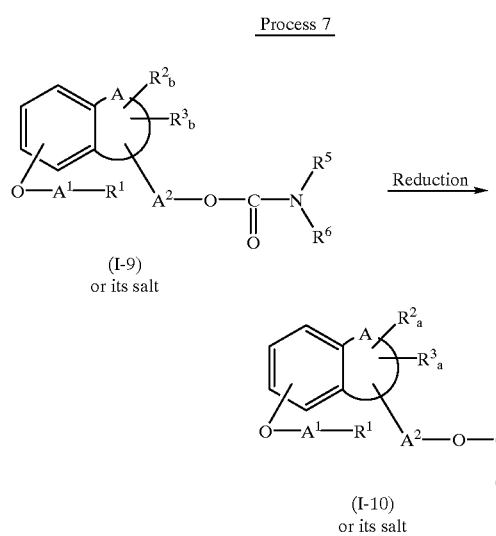

wherein $R^1$, $R^2$, $R^3$, $R^4$, $R^5$, $R^6$, A, $A^1$ and $A^2$ are each as defined above, $R^1_a$ is a protected carboxy group, $R^2_a$ and $R^3_a$ are each a hydrogen atom, $R^2_b$ and $R^3_b$ are combined together to form an oxo group,

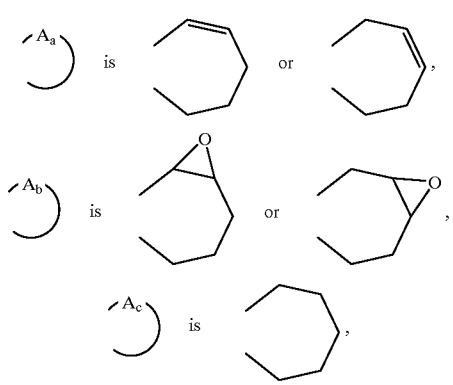

$X^1$ and $X^2$ are each a leaving group.

It is to be noted that isomerization or rearrangement of the object compounds (I) may occur due to the effect of the light, acid, base or the like, and compounds obtained as the result of said isomerization or rearrangement are also included within the scope of the present invention.

Some of the starting compounds are novel and can be prepared by following processes.

Process A

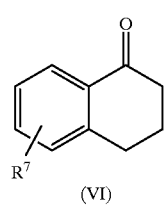

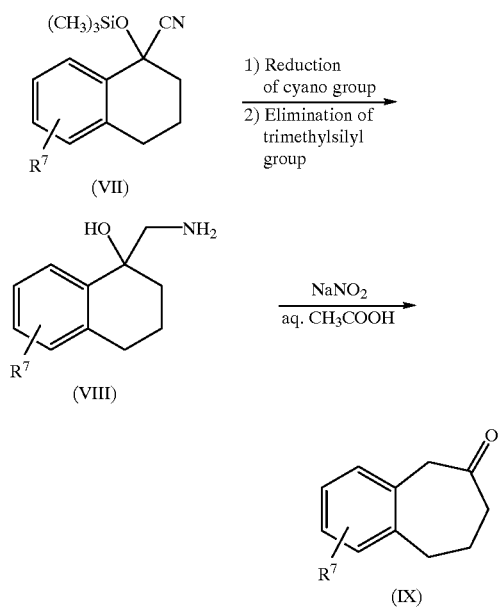

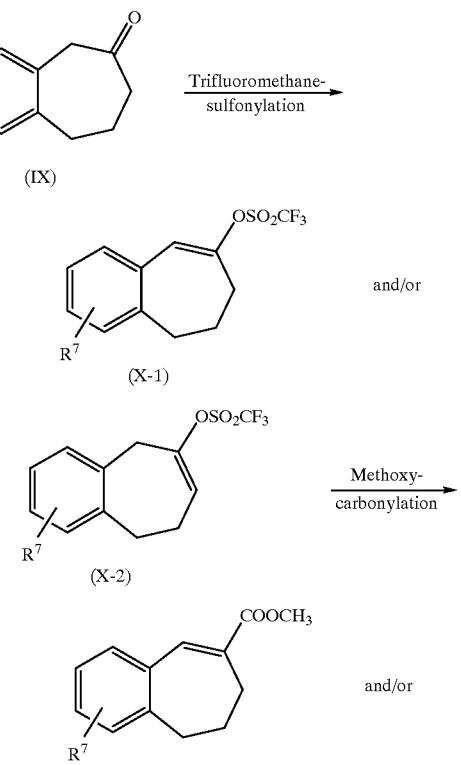

-continued

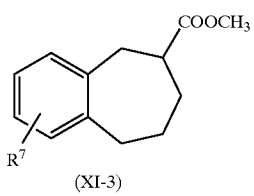
(XI-3)

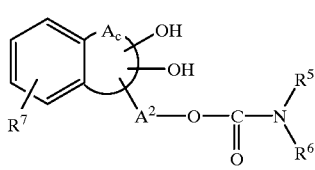
(XV)

→ Elimination of hydroxy protective group

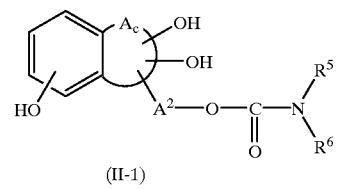
(II-1)

Process C

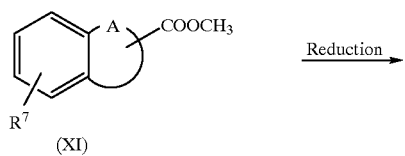
(XI)

Reduction →

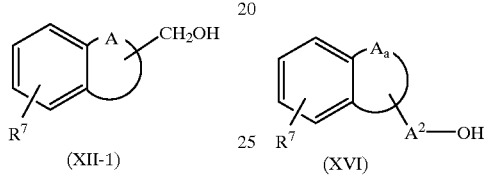
(XII-1)

Process F

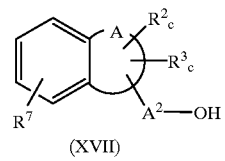
(XVI)

Addition of carbene →

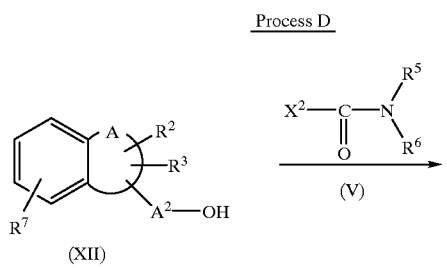
(XVII)

Process D $X^2-\overset{R^5}{\underset{\underset{O}{\|}}{C}}-\overset{}{\underset{R^6}{N}}$ (V)

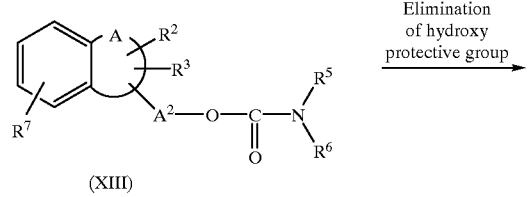
(XII)

→

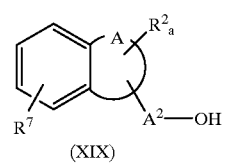
(XVIII)

Process G

Hydration →

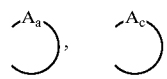
(XIX)

Elimination of hydroxy protective group →

(XIII)

(II) or its salt wherein $R^2$, $R^3$, $R^5$, $R^6$, $A^2$, $R^2_a$, A, $A_a$, $A_c$ and $X^2$ are each as defined above, $R^2_c$ and $R^3_c$ are combined together to form a lower alkylene group, $R^7$ is a protected hydroxy group.

In the above and subsequent descriptions of the present specification, suitable examples and illustrations of the various definitions which the present invention includes within the scope are explained in detail as follows.

The term "lower" is intended to mean 1 to 6 carbon atoms, unless otherwise indicated.

Process E

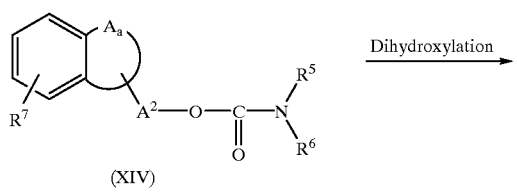
(XIV)

Dihydroxylation →

Suitable aryl groups may contain 6 to 12 carbon atoms and may be optionally substituted with suitable substituent (s) such as a halogen, amino, hydroxy, a lower alkyl, a lower alkoxy or the like. Specific examples thereof are phenyl, tolyl, xylyl, mesityl, naphthyl and the like.

Suitable lower alkylene groups may include straight or branched ones having 1 to 6 carbon atoms. Examples thereof are methylene, ethylene, trimethylene, tetramethylene, 2-methyltrimethylene, pentamethylene, hexamethylene and the like. Among them, the one having 1 to 3 carbon atoms is preferred.

Suitable lower alkyl groups may include straight or branched ones having 1 to 6 carbon atoms. Examples thereof are methyl, ethyl, propyl, isopropyl, butyl, isobutyl, sec-butyl, t-butyl, pentyl, t-pentyl, hexyl and the like. Among them, the one having 1 to 4 carbon atoms is preferred.

Suitable protected carboxy groups may include esterified carboxy groups and the like.

Suitable examples of the ester moieties of the esterified carboxy groups may include lower alkyl groups(e.g., methyl, ethyl, propyl, isopropyl, butyl, isobutyl, tert-butyl, pentyl or hexyl) which may have suitable substituent(s), for example, lower alkanoyloxy(lower)alkyl groups[e.g., acetoxymethyl, propionyloxymethyl, butyryloxymethyl, valeryloxymethyl, pivaloyloxymethyl, hexanoyloxymethyl or acetoxyethyl], halo(lower)alkyl groups (e.g., 2-iodoethyl or 2,2,2-trichloroethyl), and lower alkoxycarbonyloxy (lower)alkyl groups (e.g., methoxycarbonyloxymethyl or 2-methoxycarbonyloxyethyl); lower alkenyl groups (e.g., vinyl or allyl); lower alkynyl groups (e.g., ethynyl or propynyl); ar(lower)alkyl groups which may have suitable substituent(s) such as phenyl(lower)alkyl groups (e.g., benzyl, 4-methoxybenzyl, 4-nitrobenzyl, phenethyl, trityl, bis(methoxyphenyl)methyl, 3,4-dimethoxybenzyl or 4-hydroxy-3,5-di-tert-butylbenzyl); aryl groups which may have suitable substituent(s) (e.g., phenyl, 4-chlorophenyl, tolyl, tert-butylphenyl, xylyl, mesityl or cumenyl); and the like.

Suitable protected hydroxy groups may include lower alkoxy, ar(lower)alkoxy, acyloxy, tri(lower)alkylsilyloxy, diaryl(lower)alkylsilyloxy groups and the like.

Suitable examples of the lower alkoxy groups may include methoxy, ethoxy, tert-butoxy and the like.

Suitable examples of the ar(lower)alkoxy groups may include benzyloxy, phenethyloxy and the like.

Suitable acyl moieties in the acyloxy groups may include aliphatic acyl groups such as a lower alkanoyl (e.g., formyl, acetyl, propionyl, butyryl, isobutyryl, valeryl, isovaleryl, oxalyl, succinyl or pivaloyl), a lower alkoxycarbonyl (e.g., methoxycarbonyl or ethoxycarbonyl), a lower alkanesulfonyl (e.g., mesyl or ethanesulfonyl), an arenesulfonyl (e.g., benzenesulfonyl or tosyl); and acyl groups containing aromatic or heterocyclic ring such as an aroyl (e.g., benzoyl, toluoyl, xyloyl, naphthoyl, phthaloyl or indancarbonyl), an ar(lower)alkanoyl (e.g., phenylacetyl or phenylpropionyl), an ar(lower)alkoxycarbonyl (e.g., benzyloxycarbonyl or phenethyloxycarbonyl); and the like.

Suitable examples of the tri(lower)alkylsilyloxy groups may include trimethylsilyloxy, triethylsilyloxy, triisopropylsilyloxy, dimethylisopropylsilyloxy, tert-butyldimethylsilyloxy and the like.

Suitable examples of the diaryl(lower)alkylsilyloxy groups may include tert-butyldiphenylsilyloxy and the like.

Suitable leaving groups may include a halogen (e.g., chlorine, bromine, iodine or fluorine), a lower alkoxy (e.g., methoxy, ethoxy, propoxy, isopropoxy or butoxy), an acyloxy as exemplified above, and the like.

Preferred embodiments of the object compounds (I) are as follows:

$R^1$ is a carboxy group, or a protected carboxy group (more preferably an esterified carboxy group, most preferably a lower alkoxycarbonyl group), $R^2$ and $R^3$ are each a hydrogen atom or a hydroxy group, or $R^2$ and $R^3$ are combined together to form an oxo group or a lower alkylene group (more preferably an oxo group or a methylene group), $R^4$ is a hydrogen atom or a hydroxy group, $R^5$ and $R^6$ are each an aryl group(more preferably a phenyl group), $A^1$ and $A^2$ are each a lower alkylene group (more preferably a $C_1$–$C_3$ alkylene group, most preferably a methylene group), and

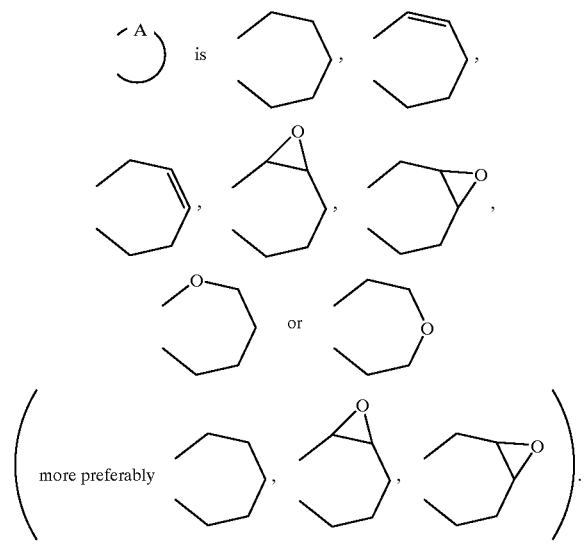

The processes for preparing the object compounds and starting compounds of the present invention are explained in detail in the following.

Process 1

A compound (I) or its salt can be prepared by reacting a compound (II) or its salt with a compound (III) or its salt.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction is usually carried out under cooling to heating since the reaction temperature is not critical.

The reaction is usually carried out in the presence of a base.

Suitable bases may include inorganic bases such as an alkaline metal hydroxide (e.g., sodium or potassium hydroxide), an alkaline earth metal hydroxide (e.g., magnesium or calcium hydroxide), an alkaline metal carbonate (e.g., sodium or potassium carbonate), an alkaline metal bicarbonate (e.g., sodium or potassium bicarbonate), an alkaline earth metal carbonate (e.g., magnesium or calcium carbonate) or the like, and organic bases such as a tri(lower) alkylamine (e.g., trimethylamine, triethylamine or diisopropylethylamine), a di(lower)alkylaniline (e.g., dimethylaniline), pyridine or the like.

Process 2

A compound (I-2) or its salt can be prepared by subjecting a compound (I-1) or its salt to an elimination of the carboxy protective group of $R^1_a$.

Suitable method of this reaction may include conventional one such as hydrolysis, reduction and the like.

(i) For Hydrolysis

The hydrolysis is preferably carried out in the presence of a base or an acid including Lewis acid.

Suitable bases may include inorganic bases such as an alkaline metal [e.g., sodium or potassium], hydroxide, carbonate or bicarbonate thereof and organic bases such as a trialkylamine [e.g., trimethylamine or triethylamine], picoline, 1,5-diazabicyclo[4.3.01]-non -5-ene, 1,4-diazabicyclo[2.2.2]octane, 1,8-diazabicyclo[5.4.0]undec-7-ene or the like.

Suitable acids may include organic acids [e.g., formic acid, acetic acid, propionic acid, trichloroacetic acid or trifluoroacetic acid] and inorganic acids [e.g., hydrochloric acid, hydrobromic acid, sulfuric acid, hydrogen chloride or hydrogen bromide]. The elimination using Lewis acid such as trihaloacetic acid [e.g., trichloroacetic acid or trifluoroacetic acid] or the like is preferably carried out in the presence of cation trapping agents [e.g., anisole or phenol].

The reaction is usually carried out in a solvent such as water, an alcohol [e.g., methanol or ethanol], methylene chloride, tetrahydrofuran, 1,2-dimethoxyethane, dioxane, a mixture thereof or any other solvent which does not adversely influence the reaction. A liquid base or acid can be also used as a solvent. The reaction is usually carried out under cooling to warming since the reaction temperature is not critical.

(ii) For Reduction

The reduction is carried out in a conventional manner, including a chemical reduction and a catalytic reduction.

Suitable reducing agents to be used in the chemical reduction are a combination of metals (e.g., tin, zinc or iron) or metallic compounds (e.g., chromium chloride or chromium acetate) and organic or inorganic acids (e.g., formic acid, acetic acid, propionic acid, trifluoroacetic acid, p-toluenesulfonic acid, hydrochloric acid or hydrobromic acid).

Suitable catalysts to be used in the catalytic reduction are conventional ones such as platinum catalysts (e.g., platinum plate, spongy platinum, platinum black, colloidal platinum, platinum oxide or platinum wire), palladium catalysts (e.g., spongy palladium, palladium black, palladium oxide, palladium on carbon, colloidal palladium, palladium on barium sulfate or palladium on barium carbonate), nickel catalysts (e.g., reduced nickel, nickel oxide or Raney nickel), cobalt catalysts (e.g., reduced cobalt or Raney cobalt), iron catalysts (e.g., reduced iron or Raney iron), copper catalysts (e.g., reduced copper, Raney copper or Ullman copper) and the like. The reduction is usually carried out in a conventional solvent which does not adversely influence the reaction such as water, methanol, ethanol, propanol, N,N-dimethylformamide, tetrahydrofuran or a mixture thereof. Additionally, in the case where the above-mentioned acid to be used in the chemical reduction is in liquid, it can also be used as a solvent.

The reaction is usually carried out under cooling to warming since the reaction temperature of this reduction is not critical.

Process 3

A compound (I) or its salt can be prepared by reacting a compound (IV) or its salt with a compound (V) or its salt.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction is usually carried out under cooling to heating since the reaction temperature is not critical.

The reaction is usually carried out in the presence of a base.

Suitable bases can be referred to those of Process 1. A liquid base can be also used as a solvent.

Process 4

A compound (I-4) or its salt can be prepared by subjecting a compound (I-3) or its salt to an epoxidation.

Epoxidation of a double bond in the compound (I-3) can be accomplished by oxidants, for example, hydrogen peroxide or its derivatives. Suitable derivatives of the hydrogen peroxide are a lower alkyl hydroperoxide (e.g., tert-butyl hydroperoxide), a peroxy acid (e.g., peroxyacetic acid, peroxytrifluoroacetic acid or m-chloroperoxybenzoic acid) or the like. Other oxidants such as dimethyldioxirane, ozone, sodium hypochlorite or the like may also be used.

This reaction is preferably carried out in the presence of a base such as an inorganic base such as an alkaline metal [e.g., sodium or potassium], hydroxide, carbonate or bicarbonate thereof and an organic base such as a trialkylamine [e.g., trimethylamine or triethylamine] or the like.

The reaction is usually carried out in a conventional solvent such as water, an alcohol (e.g., methanol, ethanol or isopropyl alcohol), tetrahydrofuran, dioxane, dichloromethane, ethylene dichloride, chloroform, N,N-dimethylformamide, N,N-dimethylacetamide or any other organic solvent which does not adversely affect the reaction.

The reaction is usually carried out under cooling to heating since the reaction temperature is not critical.

Process 5

A compound (I-6) or its salt can be prepared by reducing a compound (I-5) or its salt.

Reduction of epoxide is accomplished by (1) a catalytic hydrogenation over platinum catalyst, preferably in the presence of the acid, or (2) a chemical reduction using lithium aluminum hydride, or a complex hydride of alane or borane.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction is usually carried out under cooling to heating since the reaction temperature is not critical.

Process 6

A compound (I-8) or its salt can be prepared by oxidizing a compound (I-7) or its salt.

Oxidation of a secondary alcohol can be accomplished by an oxidizing agent, for example, sodium dichromate, pyridinium chlorochromate (Corey's reagent) or the like.

The reaction is usually carried out in a conventional solvent which does not adversely influence the reaction such as tetrahydrofuran, dichloromethane, ethylene dichloride, chloroform or a mixture thereof.

The reaction may be usually carried out under cooling to warming since the reaction temperature of this oxidation is not critical.

Process 7

A compound (I-10) or its salt can be prepared by reducing a compound (I-9) or its salt.

Reduction of ketone can be accomplished by (1) a catalytic hydrogenation over paladium catalyst under $H_2$ gas, or (2) a chemical reduction using lithium aluminum hydride or a complex hydride of alane or borane. This reaction is usually conducted in the same manner as Process 5.

Some of the starting compounds of the present invention can be prepared by the following processes A to G.

Process A

A compound (IX) can be prepared from a compound (VI) according to a method described in Preparations 1, 2 and 3 or similar method thereto.

Process B

Compounds (XI-1), (XI-2) and (XI-3) can be prepared from a compound (IX) according to a method described in Preparations 4, 5, 6 and 7 or similar method thereto.

Process C

A compound (XII-1) can be prepared by subjecting a compound (XI) to reduction.

The reduction can be carried out in accordance with a method described in the Preparations 8 and 11 or similar method thereto.

Process D

A compound (II) or its salt can be prepared by subjecting a compound (XII) to carbamoylation, followed by elimination reaction of a hydroxy protective group of $R^7$.

These reactions can be carried out in accordance with a methods described in the Preparations 9 and 10, 12 and 13, 17 and 18, 20 and 21, 22 and 23, or similar method thereto.

Process E

A compound (II-1) can be prepared by subjecting a compound (XIV) to a dihydroxylation reaction, followed by an elimination of the hydroxy protective group of $R^7$.

These reactions can be carried out in accordance with methods described in the Preparations 14 and 15 or similar methods thereto.

Process F

A compound (XVII) can be prepared by subjecting a compound (XVI) to an addition of carbene.

This reaction can be carried out in accordance with a method described in Preparation 16 or similar method thereto.

Process G

A compound (XIX) can be prepared by subjecting a compound (XVIII) to a hydration reaction.

This reaction can be carried out in accordance with a method described in Preparation 19 or similar method thereto.

The object compounds (I) of this invention and pharmaceutically acceptable salt thereof may exert pharmacological activities such as inhibitory activity on platelet aggregation, vasodilating activity, antihypertensive activity or the like, which is believed to be a prostaglandin $I_2$ agonist. Accordingly, they can be used for treating and/or preventing thrombosis, arterial obstruction (e.g., chronic arterial obstruction), cerebrovascular disease, gastric ulcer, hepatitis, hepatic insufficiency, hepatic cirrhosis, arteriosclerosis, ischemic heart disease, restenosis or ischemic complications after coronary angioplasty (e.g., PTCA or coronary stenting) hypertension, inflammation, heart failure, renal disease (e.g., renal failure or nephritis), diabetic complication (e.g., diabetic neuropathy, diabetic nephropathy or diabetic retinopathy), peripheral circulatory disturbance, and the like. Moreover, they can be also used for protecting organs after transplantation or surgery.

Further, the object compounds (I) and pharmaceutically acceptable salts thereof can be also used as a component for organ preserving fluids and as an agent for inhibiting metastasis of cancer.

Still further, the object compounds (I) may be also useful for treating and/or preventing dermatosis (e.g. chilblain, bedsore, baldness, etc.).

The patents, patent applications and publications cited herein are incorporated by reference.

In order to show the utility of the object compounds (I), pharmacological data of the representative compounds are shown in the following.

i) Inhibition of Human Platelet Aggregation Induced by ADP

[I] Test Compound (1) Sodium {[6-(N,N-diphenylcarbamoyloxy)methyl-6,7,8,9-tetrahydro-5H-benzocyclohepten-1-yl]oxy}acetate, (2) Sodium {[6-(N,N-diphenylcarbamoyloxy)methyl-6,7-epoxy-6,7,8,9-tetrahydro-5H-benzocyclohepten-1-yl]oxy}acetate.

[II] Test Method

Human blood was collected from healthy volunteers and mixed with 1/10 volume of 3.8% sodium citrate solution, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATRACER 801 (NBS, Japan), a 8 channel aggregometer. 25 μl of a solution of Test compound in Tris-acetate buffer pH7.4 and 225 μl of PRP were mixed and stirred at 1000 rpm for 2 minutes at 37° C. Aggregation was induced by ADP (adenosin 5'-diphosphate) solution at the final concentration of 2.5 μM.

[III] Test Result

| Test Compound ($1.0 \times 10^{-7}$M) | Inhibition (%) |
| --- | --- |
| (1) | >90% |
| (2) | >90% |

The pharmaceutical composition of the present invention which contains the object compound (I) or a pharmaceutically acceptable salt thereof as an active ingredient can be used in the form of a pharmaceutical preparation, for example, in solid, semisolid or liquid form (e.g. tablet, pellet, troche, capsule, suppository, cream, ointment, aerosol, powder, solution, emulsion, suspension etc.), which are suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention may contain various organic or inorganic carrier materials which are conventionally used for pharmaceutical purpose, such as excipients (e.g., sucrose, starch, mannite, sorbit, lactose, glucose, cellulose, talc, calcium phosphate or calcium carbonate), binding agents (e.g., cellulose, methyl cellulose, hydroxypropylcellulose, polypropylpyrrolidone, gelatin, gum arabic, polyethyleneglycol, sucrose or starch), disintegrators (e.g., starch, carboxymethyl cellulose, calcium salt of carboxymethyl cellulose, hydroxypropylstarch, sodium glycol-starch, sodium bicarbonate, calcium phosphate or calcium citrate), lubricants (e.g., magnesium stearate, talc or sodium laurylsulfate), flavoring agents (e.g., citric acid, mentol, glycine or orange powders), preservatives (e.g., sodium benzoate, sodium bisulfite, methylparaben or propylparaben), stabilizers (e.g., citric acid, sodium citrate or acetic acid), suspending agents (e.g., methyl cellulose, polyvinylpyrrolidone or aluminum stearate), dispersing agents, aqueous diluting agents (e.g., water), base waxes (e.g., cacao butter, polyethyleneglycol or white petrolatum).

The effective ingredient may usually be administered with a unit dose of 0.01 mg/kg to 50 mg/kg, 1 to 4 times a day. However, the above dosage may be increased or decreased according to age, weight, conditions of a patient or an administering method.

Abbreviations used in this application are as follows
THF: Tetrahydrofuran
EtOAc: Ethyl acetate
Et$_2$O: Diethyl ether
DMF: N,N-Dimethylformamide
EtOH: Ethanol
MeOH: Methanol
TMS: Trimethylsilyl
AcOH: Acetic acid
MeCN: Acetonitrile
tBuOH: tert-Butyl alcohol

BEST MODE FOR CARRING THE INVENTION

The following preparations and examples are given only for the purpose of illustrating the present invention in more detail.

Preparation 1

To a suspension of 5-(tert-butyldiphenylsilyloxy)-1,2,3,4-tetrahydronaphthalen-1-one (32.23 g) and zinc iodide (514 mg) in CH$_2$Cl$_2$ (160 ml) was added TMS-CN (15.2 ml) at room temperature. After stirring for 24 hours, the reaction mixture was washed with saturated sodium hydrogencarbonate solution, water, and then brine (a saturated sodium chloride aqueous solution). It was dried over magnesium sulfate and evaporated in vacuo to give crude 5-(tert-butyldiphenylsilyloxy)-1-trimethylsilyloxy-1,2,3,4-tetrahydronaphthalene-1-carbonitrile (40.3 g) as an oil.

IR (Neat): 2956, 2858, 1583, 1464, 1429, 1274 cm$^{-1}$

NMR (CDCl$_3$, δ): 0.19 (9H, s), 1.09 (9H, s), 1.92–2.40 (4H, m), 2.87–2.98 (2H, m), 6.38 (1H, dd, J=8.0, 1.1 Hz), 6.83 (1H, dd, J=8.0, 8.0 Hz), 7.20 (1H, d, J=8.0 Hz), 7.28–7.50 (6H, m), 7.60–7.74 (4H, m)

APCI-MASS (m/z): 401 (M+H-TMS-CN)$^+$

Preparation 2

To a suspension of lithium aluminum hydride (6.12 g) in THF (450 ml) was dropwise added a solution of crude 5-(tert-butyldiphenylsilyloxy)-1-trimethylsilyloxy-1,2,3,4-tetrahydronaphthalene-1-carbonitrile (40.3 g) in THF (300 ml) at 5° C. The mixture was stirred at the same temperature for 1 hour and then at room temperature for 2 hours. The mixture was added with a saturated potassium sodium tartrate solution under ice cooling. A resultant insoluble material was removed by filtration and washed with THF. The filtrate was evaporated to give 1-aminomethyl-5-(tert-butyldiphenylsilyloxy)-1,2,3,4-tetrahydronaphthalen-1-ol (34.8 g) as an oil.

IR (Neat): 3373, 2933, 2858, 1579, 1460, 1427, 1269 cm$^{-1}$

NMR (CDCl$_3$, δ): 1.09 (9H, s), 1.60–2.20 (4H, m), 2.70–3.10 (4H, m), 6.32 (1H d, J=7.25 Hz), 6.77 (1H, dd, J=7.5, 7.5 Hz), 7.07 (1H, d, J=7.5 Hz), 7.25–7.50 (6H, m), 7.57–7.80 (4H, m)

APCI-MASS (m/z): 414 (M+H-H$_2$O)$^+$

Preparation 3

To a solution of 1-aminomethyl-5-(tert-butyldiphenylsilyloxy)-1,2,3,4-tetrahydronaphthalen-1-ol (34.5 g) in 20% AcOH (700 ml) was added NaNO$_2$ (7.18 g) in water (60 ml) at 5° C. The mixture was stirred at the same temperature for 2.5 hours. After addition of CH$_2$Cl$_2$ (70 ml), the mixture was stirred for 30 minutes. The reaction mixture was extracted with EtOAc. The organic layer was washed with water and then brine. It was dried over magnesium sulfate and evaporated. The residue was purified by silica gel column chromatography (hexane-EtOAc 10:1) to give 1-(tert-butyldiphenylsilyloxy)-6,7,8, 9-tetrahydro-5H-benzocyclohepten-6-one (12.52 g).

IR (KBr): 2956, 2929, 2856, 1703, 1583, 1469, 1269 cm$^{-1}$

NMR (CDCl$_3$, δ): 1.11 (9H, s), 1.93–2.12 (2H, m), 2.55(2H, t, J=6.9 Hz), 3.19 (2H, t, J=6.5 Hz), 3.71 (2H, s), 6.41 (1H, dd, J=7.5, 1.8 Hz), 6.62–6.78 (2H, m), 7.27–7.50 (6H, m), 7.63–7.76 (4H, m)

APCI-MASS (m/z): 415 (M+H)$^+$

Preparation 4

To a solution of 1-(tert-butyldiphenylsilyloxy)-6,7,8,9-tetrahydro-5H-benzocyclohepten-6-one (6.52 g) and 2,6-di-tert-butyl-4-methylpyridine (4.21 g) in CH$_2$Cl$_2$ (130 ml) was added trifluoromethanesulfonic anhydride (3.18 ml). The mixture was refluxed for 4 hours. After addition of 2,6-di-tert-butyl-4-methylpyridine (2.91 g) and trifluoromethanesulfonic anhydride (2.1 ml), the mixture was refluxed for further 3 hours. After cooling, the reaction mixture was concentrated in vacuo. The resultant was added with Et$_2$O (150 ml). The resulting precipitate was removed by filtration. The filtrate was washed with 1N-hydrochloric acid, water, and then brine. It was dried over magnesium sulfate and evaporated. The residue was purified by silica gel column chromatography (hexane-EtOAc 50:1 to 25:1) to give a 2:1 mixture of 1-(tert-butyldiphenylsilyloxy)-8,9-dihydro-7H-benzocyclohepten-6-yl trifluoromethanesulfonate and 1-(tert-butyldiphenylsilyloxy)-8,9-dihydro-5H-benzocyclohepten-6-yl trifluoromethanesulfonate (7.01 g)

IR (Neat): 2958, 2933, 2860, 1577, 1462, 1415 cm$^{-1}$

NMR (CDCl$_3$, δ): 1.10 (9H, s), 1.92–2.07 and 2.37–2.52 (total 2H, m), 2.77 and 3.77 (total 2H, t, J=6.5 Hz and br s, respectively), 3.10–3.28 (2H, m), 5.68–5.78 and 6.55 (total 1H, m and s, respectively), 6.35–6.45 (1H, m), 6.62–6.78 (2H, m), 7.28–7.53 (6H, m), 7.62–7.77 (4H, m)

Preparation 5

A 2:1 mixture of 1-(tert-butyldiphenylsilyloxy)-8,9-dihydro-7H-benzocyclohepten-6-yl trifluoromethanesulfonate and 1-(tert-butyldiphenylsilyloxy)-8,9-dihydro-5H-benzocyclohepten-6-yl trifluoromethanesulfonate (7.36 g), triethylamine (3.76 ml), palladium(II) acetate (182 mg), 1,3-bis(diphenylphosphino)propane (334 mg), and MeOH (30 ml) in DMF (60 ml) was purged for 1 hour with carbon monoxide. The mixture was stirred under carbon monoxide atmosphere at 80° C. for 2.5 hours. After cooling to room temperature, the reaction mixture was diluted with EtOAc, washed with 5% KHSO$_4$ solution, water, saturated sodium hydrogencarbonate solution, water and then brine. It was dried over magnesium sulfate and evaporated in vacuo. The residue was purified by silica gel column chromatography (hexane-EtOAc 15:1) to give a 2:1 mixture of methyl 1-(tert-butyldiphenylsilyloxy)-8,9-dihydro-7H-benzocycloheptene-6-carboxylate and methyl 1-(tert-butyldiphenylsilyloxy)-8,9-dihydro-5H-benzocycloheptene-6-carboxylate (4.05 g) as an oil.

IR (Neat): 2951, 2931, 2858, 1711, 1630, 1572, 1460 cm$^{-1}$

NMR (CDCl$_3$, δ): 1.10 and 1.11 (total 9H, each s), 2.02–2.18, 2.50–2.65, and 3.75 (total 4H, m, m, and s, respectively), 2.97–3.07 and 3.25–3.35 (total 2H, each m), 3.82 (3H, s), 6.32–6.48 (1H, m), 6.60–6.88 (2H, m), 6.90–6.97 and 7.65–7.77 (total 5H, each m), 7.30–7.50 (6H, m) APCI-MASS (m/z): 457 (M+H)$^+$ Preparation 6

To a solution of a 2:1 mixture of methyl 1-(tert-butyldiphenylsilyloxy)-8,9-dihydro-7H-benzocycloheptene-6-carboxylate and methyl 1-(tert-butyldiphenylsilyloxy)-8,9-dihydro-5H-benzocycloheptene-6-carboxylate (4.02 g) in a mixed solvent of CHCl$_3$ and EtOH (1:1, 80 ml) were added RhCl₃.3H₂O (200 mg) and water (4 ml). The mixture was stirred at 70° C. for 72 hours with addition of RhCl₃.3H₂O (100 mg) every 24 hours. After cooling, the reaction mixture was evaporated and the residue was extracted with EtOAc. The organic layer was washed with 1N-hydrochloric acid, water, saturated sodium hydrogencarbonate solution, water, and then brine. It was dried over magnesium sulfate and evaporated in vacuo. The residue was purified by silica gel column chromatography (hexane-EtOAc 15:1) to give a 4:1 mixture of methyl 1-(tert-butyldiphenylsilyloxy)-8,9-dihydro-7H-benzocycloheptene-6-carboxylate and methyl 1-(tert-butyldiphenylsilyloxy)-8,9-dihydro-5H-benzocycloheptene-6-carboxylate (3.69 g) as an oil.

IR (Neat): 2952, 2931, 2858, 1711, 1630, 1572, 1460 cm⁻¹

NMR (CDCl₃, δ): 1.10 and 1.11 (total 9H, each s), 2.02–2.18, 2.50–2.65, and 3.75 (total 4H, m, m, and s, respectively), 2.97–3.07 and 3.25–3.35 (total 2H, each m), 3.82 (3H, s), 6.32–6.48 (1H, m), 6.60–6.88 (2H, m), 6.90–6.97 and 7.65–7.77 (total 5H, each m), 7.30–7.50 (6H, m) APCI-MASS (m/z): 457 (M+H)⁺

Preparation 7

To a solution of a mixture of methyl 1-(tert-butyldiphenylsilyloxy)-8,9-dihydro-7H-benzocycloheptene-6-carboxylate and methyl 1-(tert-butyldiphenylsilyloxy)-8,9-dihydro-5H-benzocycloheptene-6-carboxylate (1.50 g) in EtOAc (60 ml) was added 10% Pd-C (wet) (300 mg). The mixture was stirred under hydrogen atmosphere at room temperature for 7 hours. After removal of Pd-C by filtration, the filtrate was evaporated to give methyl 1-(tert-butyldiphenyl-silyloxy)-6,7,8,9-tetrahydro-5H-benzocycloheptene-6-carboxylate (1.51 g) as an oil.

IR (Neat): 2931, 2856, 1736, 1583, 1466, 1429, 1267 cm⁻¹

NMR (CDCl₃, δ): 1.09 (9H, s), 1.30–1.55 (1H, m), 1.80–2.28 (3H, m), 2.42–2.72 (2H, m), 2.90–3.18 (2H, m), 3.55 (1H, dd, J=14.6, 6.9 Hz), 3.68 (3H, s), 6.33 (1H, dd, J=6.7, 2.6 Hz), 6.58–6.70 (2H, m), 7.27–7.50 (6H, m), 7.62–7.77 (4H, m)

APCI-MASS (m/z): 459 (M+H)⁺

Preparation 8

To a suspension of lithium aluminum hydride (66 mg) in THF (20 ml) was added dropwise a solution of methyl 1-(tert-butyldiphenylsilyloxy)-6,7,8,9-tetrahydro-5H-benzocycloheptene-6-carboxylate (800 mg) in THF (4 ml) at 5° C. The mixture was stirred at the same temperature for 1 hour and then at room temperature for 30 minutes. The mixture was added with 1N-hydrochloric acid under ice cooling and extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 2:1) to give [1-(tert-butyldiphenylsilyloxy)-6,7,8,9-tetrahydro-5H-benzocyclohepten-6-yl]methanol (715 mg) as an oil.

IR (Neat): 3338, 2927, 2856, 1583, 1466, 1427, 1269 cm⁻¹

NMR (CDCl₃, δ): 1.09 (9H, s), 1.25–1.80 (3H, m), 1.80–2.08 (2H, m), 2.62–2.88 (3H, m), 3.38–3.53 (1H, m), 3.49 (2H, d, J=6.4 Hz), 6.32 (1H, dd, J=6.8, 2.5 Hz), 6.58–6.70 (2H, m), 7.27–7.48 (6H, m), 7.62–7.77 (4H, m)

MALDI-MASS (m/z): 453 (M+Na)⁻

Preparation 9

A mixture of [1-(tert-butyldiphenylsilyloxy)-6,7,8,9-tetrahydro-5H-benzocyclohepten-6-yl]methanol (200 mg) and diphenylcarbamoyl chloride (324 mg) in pyridine (5 ml) was stirred at 100° C. for 48 hours. After cooling, the reaction mixture was poured into 6N-hydrochloric acid (13 ml) under ice-cooling and extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 15:1 to 10:1) to give [1-(tert-butyldiphenylsilyloxy)-6,7,8,9-tetrahydro-5H-benzocyclohepten-6-yl]methyl N,N-diphenylcarbamate (262.7 mg) as an amorphous solid.

IR (KBr): 2929, 2854, 1716, 1587, 1493, 1466, 1271 cm⁻¹

NMR (CDCl₃, δ): 1.08 (9H, s), 1.25–1.60 (2H, m), 1.70–1.98 (3H, m), 2.50–2.70 (3H, m), 3.44 (1H, dd, J=14.7, 7.5 Hz), 3.90 (1H, dd, J=10.4, 7.6 Hz), 4.10 (1H, dd, J=10.4, 5.7 Hz), 6.29 (1H, d, J=7.8 Hz), 6.39 (1H, d, J=7.8 Hz), 6.58 (1H, dd, J=7.8, 7.8 Hz), 7.12–7.48 (16H, m), 7.60–7.77 (4H, m)

APCI-MASS (m/z): 626 (M+H)⁺

Preparation 10

To a solution of [1-(tert-butyldiphenylsilyloxy)-6,7,8,9-tetrahydro-5H-benzocyclohepten-6-yl]methyl N,N-diphenylcarbamate (250 mg) in THF (5 ml) was added tetrabutylammonium fluoride (1M THF solution, 0.80 ml) at 5° C. The mixture was stirred at room temperature for 1 hour. After addition of 1N-hydrochloric acid (1.5 ml) under ice-cooling, the mixture was extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 3:1) to give (1-hydroxy-6,7,8,9-tetrahydro-5H-benzocyclohepten-6-yl) methyl N,N-diphenylcarbamate (155 mg) as an oil.

IR (Neat): 3396, 2920, 2852, 1685, 1589, 1492, 1464 cm⁻¹

NMR (CDCl₃, δ) 1.20–2.00 (5H, m), 2.38–2.78 (3H, m), 2.98–3.17 (1H, m), 3.90 (1H, dd, J=10.5, 7.5 Hz), 4.09 (1H, dd, J=10.5, 5.5 Hz), 4.73 (1H, s), 6.45 (1H, d, J=7.7 Hz), 6.58 (1H, d, J=7.7 Hz), 6.88 (1H, dd, J=7.7, 7.7 Hz), 7.13–7.43 (10H, m)

APCI-MASS (m/z): 388 (M+H)⁺

Preparation 11

To a solution of a mixture of methyl 1-(tert-butyldiphenylsilyloxy)-8,9-dihydro-7H-benzocycloheptene-6-carboxylate and methyl 1-(tert-butyldiphenylsilyloxy)-8,9-dihydro-5H-benzocycloheptene-6-carboxylate (1.20 g) in CH₂Cl₂ (25 ml) was added diisobutylaluminum hydride (1.01M toluene solution, 6.5 ml) below −50° C. The mixture was stirred at the same temperature for 30 minutes. After addition of 1N-hydrochloric acid, the mixture was extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 3:1) to give a mixture of [1-(tert-butyldiphenylsilyloxy)-8,9-dihydro-7H-benzocyclohepten-6-yl]methanol and [1-(tert-butyldiphenylsilyloxy)-8,9-dihydro-5H-benzocyclohepten-6-yl]methanol (1.10 g) as an oil.

IR (Neat): 3330, 2929, 2858, 1572, 1460, 1427, 1273 cm⁻¹

NMR (CDCl₃, δ): 1.09 and 1.11 (total 9H, each s), 2.00–2.15, 2.25–2.50, and 3.48 (total 4H, m, m, and s, respectively), 2.98–3.10 and 3.23–3.35 (total 2H, m), 4.04 and 4.23 (total 2H, each s), 5.52–5.60 and 6.51 (total 1H, m and s, respectively), 6.28–6.40 (1H, m), 6.62–6.77 (2H, m), 7.30–7.48 (6H, m), 7.65–7.78 (4H, m)

APCI-MASS (m/z): 411 (M+H-H$_2$O)$^+$

Preparation 12

A mixture of [1-(tert-butyldiphenylsilyloxy)-8,9-dihydro-7H-benzocyclohepten-6-yl]methyl N,N-diphenylcarbamate and [1-(tert-butyldiphenylsilyloxy)-8,9-dihydro-5H-benzocyclohepten-6-yl]methyl N,N-diphenylcarbamate was obtained according to a similar manner to that of Preparation 9.

IR (Neat) : 3070, 2931, 2858, 1714, 1591, 1493, 1458 cm$^{-1}$

NMR (CDCl$_3$, δ): 1.08 and 1.10 (total 9H, each s), 1.87–2.08, 2.08–2.22, 2.28–2.43, and 3.31 (total 4H, m, m, m, and s, respectively), 2.90–3.02 and 3.15–3.27 (total 2H, m), 4.59 and 4.75 (total 2H, each s), 5.50–5.58 and 6.38 (total 1H, m and s, respectively), 6.23–6.40 (1H, m), 6.52–6.75 (2H, m), 7.13–7.50 (16H, m), 7.65–7.78 (4H, m)

Preparation 13

A mixture of [1-hydroxy-8,9-dihydro-7H-benzocyclohepten-6-yl]methyl N,N-diphenylcarbamate and [1-hydroxy-8,9-dihydro-5H-benzocyclohepten-6-yl]methyl N,N-diphenylcarbamate was obtained according to a similar manner to that of Preparation 10.

IR (Neat) 3394, 2927, 1685, 1591, 1493, 1458, 1389 cm$^{-1}$

NMR (CDCl$_3$, δ): 1.83–2.00, 2.06–2.20, 2.22–2.37, and 3.3 (total 4H, m, m, m, and s, respectively), 2.67–2.80 and 2.95–3.05 (total 2H, m), 4.57 and 4.74 (total 2H, each s), 4.75 and 4.81 (total 1H, each s), 5.50–5.57 and 6.38 (total 1H, m and s, respectively), 6.37–6.45 and 6.60–6.72 (total 2H, each m), 6.85–7.03 (1H, m), 7.15–7.43 (10H, m)

Preparation 14

To a solution of a mixture of [1-(tert-butyldiphenylsilyloxy)-8,9-dihydro-7H-benzocyclohepten-6-yl]methyl N,N-diphenylcarbamate and [1-(tert-butyldiphenylsilyloxy)-8,9-dihydro-5H-benzocyclohepten-6-yl]methyl N,N-diphenylcarbamate (1.21 g) in a mixed solvent of MeCN, THF and water (7:3:2, 36 ml) were added N-methylmorpholine N-oxide (457 mg) and OsO$_4$ (0.5% t-BuOH solution, 3 ml). After stirring at room temperature for 24 hours, the reaction mixture was added with an aqueous solution (6 ml) of Na$_2$SO$_3$ (740 mg), followed by stirring for 30 minutes. After removal of the organic solvent under reduced pressure, the resultant was extracted with EtOAc. The organic layer was washed with 1N-hydrochloric acid, water, saturated sodium hydrogencarbonate solution, water, and then brine. It was dried over magnesium sulfate and evaporated in vacuo. The residue was purified by silica gel column chromatography (hexane-EtOAc 3:2 to 1:1) to give a mixture of [(5SR,6SR)-1-(tert-butyldiphenylsilyloxy)-5,6-dihydroxy-6,7,8,9-tetrahydro-5H-benzocyclohepten-6-yl]methyl N,N-diphenylcarbamate and [1(6RS,7RS)-1-(tert-butyldiphenylsilyloxy)-6,7-dihydroxy-6,7,8,9-tetrahydro-5H-benzocyclohepten-6-yl]methyl N,N-diphenylcarbamate (1.18 g) as an amorphous solid.

IR (KBr) : 3446, 3070, 2931, 2858, 1716, 1587, 1493, 1468, 1269 cm$^{-1}$

NMR (CDCl$_3$, δ): 1.08 (9H, s), 1.30–3.30 (6H, m), 3.60–3.70 and 4.55 (total 1H, m and s, respectively), 3.97–4.28 (2H, m), 6.33–6.74 (3H, m), 7.15–7.48 (16H, m), 7.60–7.74 (4H, m)

APCI-MS (m/z): 658 (M+H)$^+$

Preparation 15

To a solution of a mixture of [(5SR,6SR)-1-(tert-butyldiphenylsilyloxy)-5,6-dihydroxy-6,7,8,9-tetrahydro-5H-benzocyclohepten-6-yl]methyl N,N-diphenylcarbamate and [(6RS,7RS)-1-(tert-butyldiphenylsilyloxy)-6,7-dihydroxy-6,7,8,9-tetrahydro-5H-benzocyclohepten-6-yl]methyl N,N-diphenylcarbamate (1.04 g) in THF (10 ml) was added tetrabutylammonium fluoride (1M THF solution, 2.38 ml) at 5° C. The mixture was stirred at room temperature for 1 hour. After addition of 1N-hydrochloric acid (3 ml) under ice-cooling, the mixture was extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 4:5) to give first [(5SR,6SR)-1,5,6-trihydroxy-6,7,8,9-tetrahydro-5H-benzocyclohepten-6-yl]methyl N,N-diphenylcarbamate (468.4 mg) as an amorphous solid and then [(6RS,7RS)-1,6,7-trihydroxy-6,7,8,9-tetrahydro-5H-benzocyclohepten-6-yl]methyl N,N-diphenylcarbamate (195.9 mg) as an amorphous solid.

[(5SR,6SR)-1,5,6-Trihydroxy-6,7,8,9-tetrahydro-5H-benzocyclohepten-6-yl]methyl N,N-diphenylcarbamate IR (KBr): 3398, 2927, 1695, 1589, 1493, 1466 cm$^{-1}$ NMR (CDCl$_3$, δ): 1.32–2.20 (4H, m), 2.65–3.02 (2H, m), 4.00 (1H, d, J=11.4 Hz), 4.20(1H, d, J=11.4 Hz), 4.53 (1H, s), 6.59 (1H, d, J=7.8 Hz), 6.66 (1H, d, J=7.8 Hz), 6.94 (1H, dd, J=7.8, 7.8 Hz), 7.16–7.43 (10H, m)

APCI-MS (m/z): 420 (M+H)$^+$

[(6RS,7RS)-1,6,7-trihydroxy-6,7,8,9-tetrahydro-5H-benzocyclohepten-6-yl]methyl N,N-diphenylcarbamate IR (KBr): 3398, 2927, 1695, 1589, 1493, 1466 cm$^{-1}$ NMR (CDCl$_3$, δ): 1.40–2.20 (2H, m), 2.35–2.65 (2H, m), 2.90–3.27 (2H, m), 3.57–3.72 (1H, m), 4.04 (1H, d, J=11.3 Hz), 4.13 (1H, d, J=11.3 Hz), 6.45 (1H, d, J=7.7 Hz), 6.62 (1H, d, J=7.7 Hz), 6.90 (1H, dd, J=7.7, 7.7 Hz), 7.17–7.45 (10H, m)

APCI-MS (m/z): 420 (M+H)$^+$

Preparation 16

To a solution of a mixture of [1-(tert-butyldiphenylsilyloxy)-8,9-dihydro-7H-benzocyclohepten-6-yl]methanol and [1-(tert-butyldiphenylsilyloxy)-8,9-dihydro-5H-benzocyclohepten-6-yl]methanol (891 mg) in CH$_2$Cl$_2$ (10 ml) were added Et$_2$Zn (1.0M hexane solution, 6.24 ml) and diiodomethane (0.838 ml) at –10 to –30° C. The mixture was stirred at the same temperature for 30 minutes. Then after warming to room temperature, the mixture was stirred for 8 hours. After addition of 1N-hydrochloric acid at 5° C., the resultant was extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 3:1) to give [5-(tert-butyldiphenylsilyloxy)-1,1a,2,3,4,8b-hexahydrobenzo[a]cyclopropa[c]cyclohepten-1a-yl]methanol (646.7 mg) as an amorphous solid.

IR (KBr): 3340, 3070, 2931, 2858, 1577, 1460, 1427, 1261 cm$^{-1}$

NMR (CDCl$_3$, δ): 1.40–1.70 (2H, m), 0.99 (1H, dd, J=9.0, 4.5 Hz), 1.10 (9H, s), 1.38–1.65 (1H, m), 1.85–2.27 (3H, m), 2.58–2.78 (1H, m), 3.16 (1H, d, J=10.5 Hz), 3.45 (1H, dd, J=12.9, 4.8 Hz), 4.07 (1H, d, J=10.5 Hz), 6.33 (1H, d, J=7.8 Hz), 6.69 (1H, dd, J=7.8, 7.8 Hz), 6.83 (1H, d, J=7.8 Hz), 7.20–7.50 (6H, m), 7.55–7.80 (4H, m)

MALDI-MS (m/z): 425 (M+H-H$_2$O)$^+$

Preparation 17

A mixture of [5-(tert-butyldiphenylsilyloxy)-1,1a,2,3,4,8b-hexahydrobenzo[a]cyclopropa[c]cyclohepten-1a-yl]methanol (639 mg) and diphenylcarbamoyl chloride (1.0 g) in pyridine (6 ml) was stirred at 100° C. for 22 hours. After cooling, the reaction mixture was poured into 6N-hydrochloric acid (16 ml) under ice-cooling. The resultant was extracted with EtOAc. The organic layer was washed with water, saturated sodium hydrogencarbonate solution, water, and then brine. It was dried over magnesium sulfate and evaporated in vacuo. The residue was purified by silica gel column chromatography (hexane-EtOAc 12:1 to 10:1) to give [5-(tert-butyldiphenylsilyloxy)-1,1a,2,3,4,8b-hexahydrobenzo[a]cyclopropa[c]cyclohepten-1a-yl]methyl N,N-diphenylcarbamate (782.2 mg) as an amorphous solid.

IR (KBr): 3068, 2931, 2856, 1712, 1593, 1579, 1493, 1460 cm$^{-1}$

NMR (CDCl$_3$, δ): 0.35–0.73 (2H, m), 0.95 (1H, dd, J=9.0, 4.5 Hz), 1.25–2.05 (4H, m), 2.40–2.60 (1H, m), 3.07–3.22 (1H, m), 4.11 (1H, d, J=11.3 Hz), 4.27 (1H, d, J=11.3 Hz), 6.30 (1H, d, J=7.8 Hz), 6.66 (1H, dd, J=7.8, 7.8 Hz), 6.78 (1H, d, J=7.8 Hz), 7.14–7.45 (16H, m), 7.58–7.77 (4H, m)

APCI-MS (m/z): 425 (M+H-Ph$_2$NCO$_2$H)$^+$

Preparation 18

[5-Hydroxy-1,1a,2,3,4,8b-hexahydrobenzo[a]cyclopropa[c]cyclohepten-1a-yl]methyl N,N-diphenylcarbamate was according to the similar manner to that described for the synthesis of Preparation 15.

IR (KBr): 3367, 3064, 2937, 2864, 1711, 1684, 1583, 1493, 1452 cm$^{-1}$

NMR (CDCl$_3$, δ): 0.35–0.67 (2H, m), 0.98 (1H, dd, J=9.0, 4.6 Hz), 1.20–2.00 (4H, m), 2.45–2.83 (2H, m), 4.04 (1H, d, J=11.2 Hz), 4.31 (1H, d, J=11.2 Hz), 4.62 (1H, br), 6.63 (1H, d, J=7.7 Hz), 6.85 (1H, d, J=7.7 Hz), 6.98 (1H, dd, J=7.7, 7.7 Hz), 7.14–7.44 (10H, m)

APCI-MS (m/z): 400 (M+H)$^+$

Preparation 19

To a solution of a mixture of [1-(tert-butyldiphenylsilyloxy)-8,9-dihydro-7H-benzocyclohepten-6-yl]methanol and [1-(tert-butyldiphenylsilyloxy)-8,9-dihydro-5H-benzocyclohepten-6-yl]methanol (1.10 g) in THF (10 ml) was added borane-tetrahydrofuran complex (1M THF solution, 7.71 ml) at −30 to −20° C. The mixture was stirred at the same temperature for 30 minutes, and then at room temperature for 18 hours. The reaction mixture was cooled to 5° C. After addition of borane-tetrahydrofuran complex (1M THF solution, 2.57 ml), the mixture was stirred at room temperature for 3 hours. After addition of 2N NaOH solution (2.59 ml) and 30% H$_2$O$_2$ solution (1.76 ml) at 5° C., the resultant was stirred at room temperature for 3 hours. The mixture was extracted with EtOAc. The organic layer was washed with water and then brine. It was dried over magnesium sulfate and evaporated in vacuo. The residue was purified by silica gel column chromatography (hexane-EtOAc 3:2 to 1:2) to give first (5RS,6RS)-1-(tert-butyldiphenylsilyloxy)-6-hydroxymethyl-6,7,8,9-tetrahydro-5H-benzocyclohepten-5-ol (719.8 mg) as an amorphous solid and then (6SR,7RS)-1-(tert-butyldiphenylsilyloxy)-6-hydroxymethyl-6,7,8,9-tetrahydro-5H-benzocyclohepten-7-ol (181.4 mg) as an amorphous solid.

(5RS,6RS)-1-(tert-Butyldiphenylsilyloxy)-6-hydroxymethyl-6,7,8,9-tetrahydro-5H-benzocyclohepten-5-ol IR (KBr): 3344, 3068, 2929, 2856, 1585, 1468, 1427, 1269 cm$^{-1}$ NMR (CDCl$_3$, δ): 1.09 (9H, s), 1.20–2.60 (6H, m), 3.40–3.90 (3H, m), 4.98 (1H, d, J=8.4 Hz), 6.40 (1H, d, J=7.9 Hz), 6.79 (1H, dd, J=7.9, 7.9 Hz), 7.06 (1H, d, J=7.9 Hz), 7.25–7.50 (6H, m), 7.60–7.75 (4H, m)

(6SR,7RS)-1-(tert-Butyldiphenylsilyloxy)-6-hydroxymethyl-6,7,8,9-tetrahydro-5H-benzocyclohepten-7-ol IR (KBr): 3344, 3068, 2929, 2856, 1585, 1468, 1427, 1269 cm$^{-1}$ NMR (CDCl$_3$, δ): 1.10 (9H, s), 1.38–2.70 (6H, m), 3.50–4.05 (4H, m), 6.30–6.40 (1H, m), 6.60–6.70 (2H, m), 7.30–7.55 (6H, m), 7.64–7.87 (4H, m)

Preparation 20

[(5RS,6RS)-1-(tert-Butyldiphenylsilyloxy)-5-hydroxy-6,7,8,9-tetrahydro-5H-benzocyclohepten-6-yl]methyl N,N-diphenylcarbamate was obtained according to the similar manner to that described for the synthesis of Preparation 17.

IR (KBr): 3477, 3068, 2931, 2856, 1712, 1587, 1493, 1466 cm$^{-1}$

NMR (CDCl$_3$, δ): 1.09 (9H, s), 1.30–2.08 (5H, m), 2.53–2.73 (1H, m), 3.23–3.42 (1H, m), 4.03–4.15 (1H, m), 4.40 (1H, dd, J=10.7, 5.1 Hz), 4.63 (1H, d, J=7.6 Hz), 6.37 (1H, d, J=7.6 Hz), 6.70 (1H, dd, J=7.6, 7.6 Hz), 6.78 (1H, d, J=7.6 Hz), 7.15–7.50 (16H, m), 7.60–7.75 (4H, m)

Preparation 21

[(5RS,6RS)-1,5-Dihydroxy-6,7,8,9-tetrahydro-5H-benzocyclohepten-6-yl]methyl N,N-diphenylcarbamate was obtained according to the similar manner to that described for the synthesis of Preparation 15.

IR (KBr): 3396, 3064, 2924, 1689, 1589, 1493, 1466 cm$^{-1}$

NMR (CDCl$_3$, δ): 1.30–2.10 (5H, m), 2.38–2.58 (1H, m), 2.95–3.15 (1H, m), 4.08 (1H, dd, J=10.8, 6.5 Hz), 4.39 (1H, dd, J=10.8, 5.1 Hz), 4.61 (1H, d, J=7.6 Hz), 6.66 (1H, d, J=7.8 Hz), 6.82 (1H, d, J=7.8 Hz), 7.00 (1H, dd, J=7.8, 7.8 Hz), 7.10–7.42 (10H, m)

APCI-MS (m/z): 386 (M+H-H$_2$O)$^+$

Preparation 22

[(6SR,7RS)-1-(tert-Butyldiphenylsilyloxy)-7-hydroxy-6,7,8,9-tetrahydro-5H-benzocyclohepten-6-yl]methyl N,N-diphenylcarbamate was obtained according to the similar manner to that described for the synthesis of Preparation 17.

IR (KBr): 3477, 3068, 2929, 2856, 1712, 1587, 1493, 1466 cm$^{-1}$

NMR (CDCl$_3$, δ): 1.09 (9H, s), 1.20–2.70 (6H, m), 3.42–3.70 (2H, m), 4.18 (1H, dd, J=11.0, 4.2 Hz), 4.48 (1H, dd, J=11.0, 5.0 Hz), 6.31 (1H, d, J=7.7 Hz), 6.48 (1H, d, J=7.7 Hz), 6.62 (1H, dd, J=7.7, 7.7 Hz), 7.17–7.48 (16H, m), 7.62–7.78 (4H, m)

APCI-MS (m/z): 642 (M+H)$^+$

Preparation 23

[(6SR,7RS)-1,7-Dihydroxy-6,7,8,9-tetrahydro-5H-benzocyclohepten-6-yl]methyl N,N-diphenylcarbamate was obtained according to the similar manner to that described for the synthesis of Preparation 15.

IR (KBr): 3400, 3064, 2922, 1689, 1591, 1493, 1466 cm$^{-1}$

NMR (CDCl$_3$, δ): 1.30–2.73 (6H, m), 3.18 (1H, dd, J=14.0, 8.7 Hz), 3.52–3.68 (1H, m), 4.18 (1H, dd, J=11.0, 4.2 Hz), 4.47 (1H, dd, J=11.0, 5.1 Hz), 6.54 (1H, d, J=7.7 Hz), 6.60 (1H, d, J=7.7 Hz), 6.91 (1H, dd, J=7.7, 7.7 Hz), 7.13–7.43 (10H, m)

APCI-MS (m/z): 404 (M+H)$^+$

EXAMPLE 1

To a mixture of [1-hydroxy-6,7,8,9-tetrahydro-5H-benzocyclohepten-6-yl]methyl N,N-diphenylcarbamate (154 mg) and potassium carbonate (166 mg) in DMF (5 ml) was added ethyl bromoacetate (0.133 ml) and stirred at 40° C. for 2 hours. The reaction mixture was diluted with EtOAc, washed with water and brine. It was dried over magnesium sulfate and evaporated in vacuo. The residue was purified by silica gel column chromatography (hexane-EtOAc 3:1) to give ethyl {[6-(N,N-diphenylcarbamoyloxy)-methyl-6,7,8,9-tetrahydro-5H-benzocyclohepten-1-yl]oxy}acetate (156.2 mg) as a solid.

IR (KBr): 2902, 2850, 1755, 1711, 1587, 1493, 1308 cm$^{-1}$

NMR (CDCl$_3$, δ): 1.29 (3H, t, J=7.1 Hz), 1.25–1.62 (2H, m), 1.62–1.97 (3H, m), 2.40–2.73 (3H, m), 3.29 (1H, dd, J=14.6, 7.9 Hz), 3.90 (1H, dd, J=10.5, 7.5 Hz), 4.08 (1H, dd, J=10.5, 5.5 Hz), 4.25 (2H, q, J=7.1 Hz), 4.57 (2H, s), 6.52 (1H, d, J=7.8 Hz), 6.60 (1H, d, J=7.8 Hz), 6.96 (1H, dd, J=7.8, 7.8 Hz), 7.12–7.42 (10H, m)

APCI-MASS (m/z): 474 (M+H)$^+$

EXAMPLE 2

A mixture of ethyl {[(6-(N,N-diphenylcarbamoyloxy) methyl-8,9-dihydro-7H-benzocyclohepten-1-yl]oxy}acetate and ethyl {[6-(N,N-diphenylcarbamoyloxy)methyl-8,9-dihydro-5H-benzocyclo-hepten-1-yl]oxy}acetate was obtained according to a similar manner to that of Example 1.

IR (KBr): 2976, 1757, 1712, 1672, 1493, 1304 cm$^{-1}$

NMR (CDCl$_3$, δ): 1.29 (3H, t, J=7.1 Hz), 1.83–2.02, 2.05–2.38, and 3.31 (total 4H, m, m, and s, respectively), 2.78–2.90 and 3.05–3.13 (total 2H, m), 4.24 and 4.26 (total 2H, each q, J=7.1 Hz), 4.57, 4.60, and 4.74 (total 4H, each s), 5.48–5.54 and 6.37 (total 1H, m and s, respectively), 6.42–6.50 and 6.60–6.77 (total 2H, each m), 6.92–7.12 (1H, m), 7.12–7.42 (10H, m)

MALDI-MASS (m/z): 494 (M+Na)$^+$

EXAMPLE 3

To a mixture of ethyl {[6-(N,N-diphenylcarbamoyloxy)-methyl-8,9-dihydro-7H-benzocyclohepten-1-yl]oxy}acetate and ethyl {[6-(N,N-diphenylcarbamoyloxy)methyl-8,9-dihydro-5H -benzocyclohepten-1-yl]oxy}acetate (400 mg) and sodium carbonate (180 mg) in CH$_2$Cl$_2$ (15 ml) was added m-chloroperbenzoic acid (275 mg) at 5° C. The mixture was stirred at the same temperature for 30 minutes and then at room temperature for 2 hours. The reaction mixture was diluted with EtOAc, washed with water, saturated sodium hydrogencarbonate solution, water, and then brine. It was dried over magnesium sulfate and evaporated in vacuo. The residue was purified by silica gel column chromatography (hexane-EtOAc 3:1) to give a mixture of ethyl {[6-(N,N-diphenylcarbamoyloxy)methyl-5,6-epoxy-6, 7,8,9-tetrahydro -5H-benzocyclohepten-1-yl]oxy}acetate and ethyl {[6-(N,N-diphenylcarbamoyloxy)methyl-6,7-epoxy-6,7,8,9-tetrahydro-5H-benzocyclohepten-1-yl] oxy}acetate (365.7 mg) as an oil.

IR (Neat): 2937, 1757, 1714, 1587, 1493, 1452 cm$^{-1}$

NMR (CDCl$_3$, δ): 0.98–3.30 and 3.85 (total 7H, m and s, respectively), 1.28 and 1.29 (total 3H, each t, J=7.1 Hz), 4.02–4.53 (4H, m), 4.59 and 4.61 (total 2H, each s), 6.60–6.73 and 6.99–7.40 (total 13H, each m)

APCI-MASS (m/z): 488 (M+H)$^+$

EXAMPLE 4

To a solution of a mixture of ethyl {[6-(N,N-diphenyl-carbamoyloxy)methyl-5,6-epoxy-6,7,8,9-tetrahydro-5H-benzo-cyclohepten-5-yl]oxy}acetate and ethyl {[6-(N,N-diphenyl-carbamoyloxy) methyl-6,7-epoxy-6,7,8,9-tetrahydro-5H-benzo-cyclohepten-1-yl]oxy}acetate (265 mg) in EtOAc (13 ml) was added 10% Pd—C (wet) (80 mg). The mixture was stirred under hydrogen atmosphere at room temperature for 6 hours. After removal of the catalyst by filtration, the filtrate was evaporated. The residue was purified by silica gel column chromatography (hexane-EtOAc 2:1 to 1:1) to give ethyl {[6-(N,N-diphenylcarbamoyloxy) methyl-6-hydroxy-6,7,8,9-tetrahydro-5H-benzocyclohepten-1-yl]oxy}acetate (193.3 mg) as a solid and ethyl {[6-(N,N-diphenylcarbamoyloxy) methyl-6,7-epoxy-6,7,8,9-tetrahydro-5H-benzocyclohepten-1-yl] oxy}acetate (60.0 mg) as an oil.

Ethyl {[6-(N,N-diphenylcarbamoyloxy)methyl-6-hydroxy -6,7,8,9-tetrahydro-5H-benzocyclohepten-1-yl] oxy}acetate IR (KBr): 3491, 2914, 1757, 1695, 1587, 1495 cm$^{-1}$ NMR (CDCl$_3$, δ): 1.29 (3H, t, J=7.1 Hz), 1.38–1.85 (4H, m), 2.72 (1H, d, J=13.8 Hz), 2.75–3.05 (3H, m), 3.89 (1H, d, J=11.0 Hz), 4.02 (1H, d, J=11.0 Hz), 4.25 (2H, q, J=7.1 Hz), 4.58 (2H, s), 6.45 (1H, d, J=7.8 Hz), 6.64 (1H, d, J=7.8 Hz), 6.97 (1H, dd, J=7.8, 7.8 Hz), 7.17–7.44 (10H, m)

APCI-MASS (m/z): 490 (M+H)$^+$

Ethyl {[6-(N,N-diphenylcarbamoyloxy)methyl-6,7-epoxy-6,7,8,9-tetrahydro-5H-benzocyclohepten-1-yl] oxy}acetate IR (Neat): 2979, 2910, 1757, 1714, 1589, 1493 cm$^{-1}$ NMR (CDCl$_3$, δ): 1.29 (3H, t, J=7.1 Hz), 1.75–2.00 (1H, m), 2.23–2.50 (2H, m), 2.79–2.88 (1H, m), 2.90–3.17 (3H, m), 4.07 (1H, d, J=11.9 Hz), 4.25 (2H, q, J=7.1 Hz), 4.35 (1H, d, J=11.9 Hz), 4.61 (2H, s), 6.58–6.72 (2H, m), 7.03 (1H, dd, J=7.8, 7.8 Hz), 7.05–7.40 (10H, m)

APCI-MASS (m/z): 488 (M+H)$^+$

EXAMPLE 5

To a mixture of [(5SR,6SR)-1,5,6-trihydroxy-6,7,8,9-tetrahydro-5H-benzocyclohepten-6-yl]methyl N,N-diphenylcarbamate (461 mg) and potassium carbonate (304 mg) in DMF (8 ml) was added ethyl bromoacetate (0.244 ml) and stirred at room temperature for 18 hours. The reaction mixture was diluted with EtOAc, washed with water and then brine. It was dried over magnesium sulfate and evaporated in vacuo. The residue was purified by silica gel column chromatography (hexane-EtOAc 4:5) to give ethyl {[(5SR,6SR)-6-(N,N-diphenylcarbamoyloxy)methyl-5,6-dihydroxy-6,7,8,9-tetrahydro-5H-benzocyclohepten-1 -yl]oxy}acetate (459.6 mg) as an amorphous solid.

IR (KBr): 3464, 2937, 1757, 1716, 1587, 1493 cm$^{-1}$

NMR (CDCl$_3$, δ): 1.29 (3H, t, J=7.1 Hz), 1.35–2.15 (4H, m), 2.73–3.15 (2H, m), 4.02 (1H, d, J=11.4 Hz), 4.23 (1H, d, J=11.4 Hz), 4.25 (2H, q, J=7.1 Hz), 4.57 (3H, s), 6.71 (2H, d, J=8.0 Hz), 7.04 (1H, dd, J=8.0, 8.0 Hz), 7.18–7.43 (10H, m)

APCI-MS (m/z): 488 (M+H-H$_2$O)$^+$

EXAMPLE 6

Ethyl {[(6RS,7RS)-6-(N,N-diphenylcarbamoyloxy) methyl-6,7-dihydroxy-6,7,8,9-tetrahydro-5H-benzocyclohepten-1-yl]oxy}acetate was obtained according to the similar manner to that described for the synthesis of Example 5.

IR (KBr): 3491, 3398, 2929, 1751, 1697, 1589, 1493 cm$^{-1}$

NMR (CDCl$_3$, δ): 1.29 (3H, t, J=7.1 Hz), 1.60–2.10 (2H, m), 2.40–2.80 (2H, m), 3.03–3.27 (2H, m), 3.60–3.73 (1H, m), 4.04 (1H, d, J=11.2 Hz), 4.13 (1H, d, J=11.2 Hz), 4.25 (2H, q, J=7.1 Hz), 4.58 (2H, s), 6.51 (1H, d, J=7.8 Hz), 6.64 (1H, d, J=7.8 Hz), 6.98 (1H, dd, J=7.8, 7.8 Hz), 7.18–7.45 (10H, m)

APCI-MS (m/z): 506 (M+H)$^+$

EXAMPLE 7

Ethyl (1a-diphenylcarbamoyloxymethyl-1,1a,2,3,4,8b-hexahydrobenzo[a]cyclopropa[c]cyclohepten-5-yloxy)

acetate was obtained according to the similar manner to that described for the synthesis of Example 5.

IR (Neat): 3064, 2939, 2862, 1759, 1712, 1595, 1579, 1493, 1452 cm$^{-1}$

NMR (CDCl$_3$, δ): 0.35–0.65 (2H, m), 0.98 (1H, dd, J=9.0, 4.6 Hz), 1.25–1.48 (1H, m), 1.28 (3H, t, J=7.1 Hz), 1.60–2.00 (3H, m), 2.40–2.60 (1H, m), 3.11 (1H, dd, J=13.6, 5.0 Hz), 4.00 (1H, d, J=11.3 Hz), 4.25 (2H, q, J=7.1 Hz), 4.36 (1H, d, J=11.3 Hz), 4.58 (2H, s), 6.62 (1H, d, J=7.7 Hz), 6.92 (1H, d, J=7.7 Hz), 7.05 (1H, dd, J=7.7, 7.7 Hz), 7.13–7.40 (10H, m)

APCI-MS (m/z): 486 (M+H)$^+$

EXAMPLE 8

Ethyl {[(5RS,6RS)-6-(N,N-diphenylcarbamoyloxy) methyl-5-hydroxy-6,7,8,9-tetrahydro-5H-benzocyclohepten-1-yl]oxy}acetate was obtained according to the similar manner to that described for the synthesis of Example 5.

IR (Neat): 3483, 2929, 1757, 1712, 1587, 1493, 1468, 1394 cm$^{-1}$

NMR (CDCl$_3$, δ): 1.29 (3H, t, J=7.1 Hz), 1.30–2.05 (5H, m), 2.40–2.59 (1H, m), 3.15–3.32 (1H, m), 4.10 (1H, dd, J=10.8, 6.3 Hz), 4.25 (2H, q, J=7.1 Hz), 4.42 (1H, dd, J 10.8, 4.9 Hz), 4.58 (2H, s), 4.63 (1H, d, J=7.8 Hz), 6.69 (1H, d, J=7.8 Hz), 6.94 (1H, d, J=7.8 Hz),7.10 (1H, dd, J=7.8, 7.8 Hz), 7.15–7.43 (10H, m)

APCI-MS (m/z): 472 (M+H-H$_2$O)$^+$

EXAMPLE 9

Ethyl {[(6SR,7RS)-6-(N,N-diphenylcarbamoyloxy) methyl-7-hydroxy-6,7,8,9-tetrahydro-5H-benzocyclohepten-1-yl]oxy}acetate was obtained according to the similar manner to that described for the synthesis of Example 5.

IR (Neat): 3483, 2925, 1757, 1712, 1589, 1493, 1468, 1454 cm$^{-1}$

NMR (CDCl$_3$, δ) 1.29 (3H, t, J=7.1 Hz), 1.30–2.22 (3H, m), 2.25–2.73 (3H, m), 3.37 (1H, dd, J=14.9, 8.0 Hz), 3.50–3.67 (1H, m), 4.10–4.25 (1H, m), 4.25 (2H, q, J=7.1 Hz), 4.45 (1H, dd, J=10.9, 5.2 Hz), 4.59 (2H, s), 6.61 (1H, d, J=7.9 Hz), 6.62 (1H, d, J=7.9 Hz), 7.00 (1H, dd, J=7.9, 7.9 Hz), 7.15–7.42 (10H, m)

APCI-MS (m/z): 472 (M+H-H$_2$O)$^+$

EXAMPLE 10

To a solution of oxalyl chloride (0.052 ml) in CH$_2$Cl$_2$ (10 ml) was added a solution of DMSO (0.084 ml) in CH$_2$Cl$_2$ (0.5 ml) keeping the temperature below −55° C. The mixture was stirred for 20 minutes. After addition of a solution of ethyl {[(6RS,7RS)-6-(N,N-diphenylcarbamoyloxy)methyl-6,7-dihydroxy-6,7,8,9-tetrahydro-5H-benzocyclohepten-1-yl]oxy}acetate (150 mg) in CH$_2$Cl$_2$ (3 ml) at the same temperature, the mixture was stirred for 30 minutes. After addition of Et$_3$N (0.33 ml), the mixture was warmed to room temperature over 30 minutes. After stirring for 1 hour at the same temperature, the mixture was diluted with EtOAc, washed with 1N-hydrochloric acid, water, saturated sodium hydrogencarbonate solution, water, and then brine. It was dried over magnesium sulfate and then evaporated. The residue was purified by silica gel column chromatography (hexane-EtOAc 5:2) to give ethyl {[6-(N,N-diphenylcarbamoyloxy)methyl-6-hydroxy-7-oxo-6,7,8,9-tetrahydro-5H-benzocyclohepten-1-yl]oxy}acetate (97.2 mg) as a solid.

IR (KBr): 3458, 2985, 1757, 1728, 1585, 1493, 1469, 1383 cm$^{-1}$

NMR (CDCl$_3$, δ): 1.29 (3H, t, J=7.1 Hz), 2.38–2.86 (3H, m), 2.86 (1H, d, J=14.4 Hz), 3.01 (1H, d, J=14.4 Hz), 3.35–3.55 (1H, m), 4.03 (1H, d, J=11.4 Hz), 4.13 (1H, d, J=11.4 Hz), 4.26 (2H, q, J=7.1 Hz), 4.61 (2H, s), 6.70 (1H, d, J=7.9 Hz), 6.72 (1H, d, J=7.9 Hz), 7.10 (1H, dd, J=7.9, 7.9 Hz), 7.10–7.40 (10H, m)

APCI-MS (m/z): 504 (M+H)$^+$

EXAMPLE 11

To a solution of ethyl {[(5RS,6RS)-6-(N,N-diphenylcarbamoyloxy)methyl-5-hydroxy-6,7,8,9-tetrahydro-5H-benzocyclohepten-1-yl]oxy}acetate (179 mg) in CHCl$_3$ (15 ml) was added activated MnO$_2$ (636 mg). The mixture was refluxed for 30 minutes. Then after addition of activated MnO$_2$ (636 mg), the mixture was refluxed for 1.5 hours. Furthermore, the mixture was added with activated MnO$_2$ (636 mg) and then refluxed for 1 hour. After cooling, the mixture was filtered. The filtrate was evaporated in vacuo. The residue was purified by silica gel column chromatography (hexane-EtOAc 2:1) to give ethyl {[6-(N,N-diphenylcarbamoyloxy) methyl-5-oxo-6,7,8,9-tetrahydro-5H-benzocyclohepten-1-yl]oxy}acetate (151.1 mg) as an oil.

IR (Neat): 3064, 2937, 2864, 1757, 1714, 1593, 1493, 1460, 1383 cm$^{-1}$

NMR (CDCl$_3$, δ): 1.30 (3H, t, J=7.1 Hz), 1.40–2.15 (4H, m), 2.50–2.70 (1H, m), 3.02–3.22 (1H, m), 3.36–3.56 (1H, m), 4.20–4.40 (1H, m), 4.27 (2H, q, J=7.1 Hz), 4.50–4.63 (1H, m), 4.64 (2H, s), 6.85 (1H, d, J=7.9 Hz), 7.03–7.40 (12H, m)

APCI-MS (m/z): 488 (M+H)$^+$

EXAMPLE 12

To a solution of ethyl {[6-(N,N-diphenylcarbamoyloxy) methyl-5-oxo-6,7,8,9-tetrahydro-5H-benzocyclohepten-1-yl]oxy}acetate (100 mg) in a mixed solvent of THF and EtOH (1:4, 5 ml) were added 20% Pd(OH)$_2$ on carbon and catalytic amount of concentrated hydrochloric acid. The mixture was hydrogenated for 5 hours at 3 atm. After removal of the catalyst by filtration, the filtrate was evaporated. The residue was dissolved in EtOAc, washed with saturated sodium hydrogencarbonate solution, water, and then brine. It was dried over magnesium sulfate and evaporated in vacuo. The residue was purified by silica gel column chromatography (hexane-EtOAc 2:1) to give ethyl {[(5SR,6RS)-6-(N,N-diphenylcarbamoyloxy) methyl-5-hydroxy-6,7,8,9-tetrahydro-5H-benzocyclohepten-1-yl]oxy}acetate (22.0 mg) as an amorphous solid.

IR (KBr): 3438, 2927, 1761, 1712, 1682, 1587, 1493 cm$^{-1}$

NMR (CDCl$_3$, δ): 1.29 (3H, t, J=7.1 Hz), 1.40–2.28 (5H, m), 2.60–2.85 (1H, m), 3.13–3.33 (1H, m), 3.90–4.10 (2H, m), 4.25 (2H, q, J=7.1 Hz), 4.58 (2H, s), 4.82 (1H, s), 6.65–6.75 (2H, m), 7.06 (1H, dd, J=7.8, 7.8 Hz), 7.15–7.45 (10H, m)

APCI-MS (m/z): 472 (M+H-H$_2$O)$^+$

EXAMPLE 13

To a solution of ethyl {[6-(N,N-diphenylcarbamoyloxy)-methyl-6,7,8,9-tetrahydro-5H-benzocyclohepten-1-yl] oxy}acetate (140 mg) in a mixed solvent of MeOH and 1,4-dioxane (1:1, 6 ml) was added 1N sodium hydroxide solution (0.296 ml) at 5° C. The mixture was stirred at room temperature for 1 hour. The reaction mixture was evaporated, followed by addition of Et$_2$O. The resulting solid was collected by filtration to give sodium {[6-(N,N-diphenylcarbamoyl-oxy)methyl-6,7,8,9-tetrahydro-5H-benzocyclohepten-1-yl]oxy}-acetate (137.5 ma).

IR (KBr): 3396, 2916, 1714, 1597, 1493, 1323 cm$^{-1}$

NMR (DMSO-d$_6$, δ): 1.05–1.85 (5H, m), 2.27–2.65 (3H, m), 3.10–3.28 (1H, m), 3.75–4.00 (2H, m), 4.04 (2H, s), 6.37 (1H, d, J=7.8 Hz), 6.56 (1H, d, J=7.8 Hz), 6.87 (1H, dd, J=7.8, 7.8 Hz), 7.20–7.48 (10H, m)

MALDI-MASS (m/z): 468 (M+H)$^+$

EXAMPLE 14

The following compounds described in (1) to (4) were synthesized according to a similar manner to that of Example 13.

(1) A mixture of sodium {[6-(N,N-diphenylcarbamoyloxy)-methyl-8,9-dihydro-7H-benzocyclohepten-1-yl]oxy}acetate and sodium {16-(N,N-diphenylcarbamoyloxy)methyl-8,9-dihydro-5H-benzocyclohepten-1-yl]oxy}acetate IR (KBr) 3365, 3064, 2927, 1714, 1597, 1493, 1456 cm$^{-1}$ NMR (CDCl$_3$, δ) 1.70–1.87, 2.04–2.24, and 3.24 (total 4H, m, m, and s, respectively), 2.68–2.80 and 2.90–3.03 (total 2H, m), 4.07 (2H, s), 4.47 and 4.66 (total 2H, each s), 5.40–5.47 and 6.32 (total 1H, m and s, respectively), 6.30–6.35 and 6.55–6.67 (total 2H, each m), 6.82–7.04 (1H, m), 7.20–7.50 (10H, m)

MALDI-MASS (m/z): 466 (M+H)$^+$ (2) A mixture of sodium {[6-(N,N-diphenylcarbamoyloxy)-methyl-5,6-epoxy-6,7,8,9-tetrahydro-5H-benzocyclohepten-1-yl]oxy}acetate and sodium {[6-(N,N-diphenylcarbamoyloxy)methyl -6,7-epoxy-6,7,8,9-tetrahydro-5H-benzocyclo-hepten-1 -yl]oxy}acetate IR (KBr): 3398, 1714, 1597, 1493, 1423 cm$^{-1}$ NMR (DMSO-d$_6$, δ): 1.80–3.45 and 3.86 (total 7H, m and s, respectively), 3.85–4.48 (2H, m), 4.07 (2H, s), 6.48–7.13 (3H, m), 7.13–7.48 (10H, m)

MALDI-MASS (m/z): 482 (M+H)$^+$ (3) Sodium {[6-(N,N-diphenylcarbamoyloxy)methyl-6-hydroxy-6,7,8,9-tetrahydro-5H-benzocyclohepten-1-yl]oxy}acetate IR (KBr): 3485, 2924, 1703, 1597, 1493, 1417 cm$^{-1}$ NMR (DMSO-d$_6$, δ): 1.15–1.75 (4H, m), 2.50–2.90 (4H, m), 3.67 (1H, d, J=10.8 Hz), 3.89 (1H, d, J=10.8 Hz), 4.02 (2H, s), 4.41 (1H, br s), 6.15 (1H, d, J=7.8 Hz), 6.55 (1H, d, J=7.8 Hz), 6.80 (1H, dd, J=7.8, 7.8 Hz), 7.20–7.47 (10H, m)

MALDI-MASS (m/z): 484 (M+H)$^+$ (4) Sodium {[6-(N,N-diphenylcarbamoyloxy)methyl-6,7-epoxy-6,7,8,9-tetrahydro-5H-benzocyclohepten-6-yl]oxy}acetate IR (KBr): 3396, 1712, 1597, 1493, 1306 cm$^{-1}$ NMR (DMSO-d$_6$, δ): 1.65–1.88 (1H, m), 2.02–2.40 (2H, m), 2.77–3.10 (4H, m), 3.92 (1H, d, J=11.7 Hz), 4.08 (2H, s), 4.27 (1 H, d, J=11.7 Hz), 6.52 (1H, d, J=7.8 Hz), 6.62 (1H, d, J=7.8 Hz), 6.94 (1H, dd, J=7.8, 7.8 Hz), 7.19–7.48 (10H, m)

MALDI-MASS (m/z): 482 (M+H)$^+$

EXAMPLE 15

To a solution of ethyl {[(5SR,6SR)-6-(N,N-diphenylcarbamoyloxy)methyl-5,6-dihydroxy-6,7,8,9-tetrahydro -5H-benzocyclohepten-1-yl]oxy}acetate (70 mg) in a mixture of MeOH and 1,4-dioxane (1:1, 4 ml) was added 1N sodium hydroxide solution (0.138 ml) at 5° C. The mixture was stirred at room temperature for 1.5 hours. The reaction mixture was evaporated followed by addition of Et$_2$O. The resulting solid was collected by filtration to give sodium {[(5SR,6SR)-6-(N,N-diphenylcarbamoyloxy) methyl-5,6-dihydroxy-6,7,8,9-tetrahydro -5H-benzocyclohepten-1-yl]oxy}acetate (65.8 mg).

IR (KBr): 3410, 2927, 1699, 1597, 1493, 1415 cm$^{-1}$

NMR (DMSO-d$_6$, δ): 1.10–2.00 (4H, m), 2.74–3.25 (2H, m), 3.60–4.60 (3H, m), 4.01 (2H, s), 6.35–7.10 (3H, m), 7.20–7.48 (10H, m)

MALDI-MS (m/z): 500 (M+H)$^+$

EXAMPLE 16

Sodium {[(6RS,7RS)-6-(N,N-diphenylcarbamoyloxy) methyl-6,7-dihydroxy-6,7,8,9-tetrahydro-5H-benzocyclohepten-1-yl]oxy}-acetate was obtained according to the similar manner to that described for the synthesis of Example 15.

IR (KBr): 3410, 2927, 1699, 1595, 1493 cm$^{-1}$

NMR (DMSO-d$_6$, δ): 1.40–4.40 (9H, m), 4.02 (2H, s), 6.20–6.93 (3H, m), 7.17–7.48 (10H, m)

MALDI-MS (m/z): 500 (M+H)$^+$

EXAMPLE 17

Sodium {[6-(N,N-diphenylcarbamoyloxy)methyl-6-hydroxy -7-oxo-6,7,8,9-tetrahydro-5H-benzocyclohepten-1-yl]oxy}acetate was obtained according to the similar manner to that described for the synthesis of Example 15.

IR(KBr): 3435, 1711, 1595, 1493, 1417cm$^{-1}$

NMR (DMSO-d$_6$, δ): 2.30–3.50 (6H, m), 3.97 (1H, d, J=11.1 Hz), 4.06 (1H, d, J=11.1 Hz), 4.07 (2H, s), 6.49 (1H, d, J=7.8 Hz), 6.66 (1H, d, J=7.8 Hz), 6.97 (1H, d, J=7.8, 7.8 Hz), 7.15–7.45 (10H, m)

MALDI-MS (m/z): 498 (M+H)$^+$

EXAMPLE 18

Sodium (1a-diphenylcarbamoyloxymethyl-1,1a,2,3,4,8b -hexahydrobenzo[a]cyclopropa[c]cyclohepten-5-yloxy) acetate was obtained according to the similar manner to that described for the synthesis of Example 15.

IR (KBr): 3400, 3064, 2935, 2862, 1712, 1601, 1493, 1452, 1425 cm$^{-1}$

NMR (DMSO-d$_6$, δ): 0.25–0.55 (2H, m), 0.87–1.35 (2H, m), 1.53–1.98 (3H, m), 2.27–2.52 (1H, m), 2.90–3.10 (1H, m), 3.90 (1H, d, J=11.3 Hz), 4.03 (2H, s), 4.29 (1H, d, J=11.3 Hz), 6.58 (1H, d, J=7.8 Hz), 6.70 (1H, d, J=7.8 Hz), 6.95 (1H, dd, J=7.8, 7.8 Hz), 7.18–7.45 (10H, m)

MALDI-MS (m/z): 480 (M+H)$^+$

EXAMPLE 19

Sodium {[(5RS,6RS)-6-(N,N-diphenylcarbamoyloxy) methyl-5-hydroxy-6,7,8,9-tetrahydro-5H-benzocyclohepten-1-yl]oxy}acetate was obtained according to the similar manner to that described for the synthesis of Example 15.

IR (KBr): 3433, 2924, 1711, 1595, 1493, 1408 cm$^{-1}$

NMR (DMSO-d$_6$, δ) 1.10–1.90 (5H, m), 2.28–2.58 (1H, m), 2.90–3.15 (1H, m), 3.90–4.22 (2H, m), 4.04 (2H, s), 4.45 (1H, d, J=7.8 Hz), 5.24 (1H, br), 6.62 (1H, d, J=7.8 Hz), 6.76 (1H, d, J=7.8 Hz), 6.97 (1H, dd, J=7.8, 7.8 Hz), 7.17–7.48 (10H, m)

MALDI-MS (m/z): 484 (M+H)⁺

EXAMPLE 20

Sodium {[(5SR,6RS)-6-(N,N-diphenylcarbamoyloxy) methyl-5-hydroxy-6,7,8,9-tetrahydro-5H-benzocyclohepten-1-yl]oxy}acetate was obtained according to the similar manner to that described for the synthesis of Example 15.

IR(KBr):3446, 2925, 1711, 1593, 1493, 1469, 1458, 1419 cm⁻¹

NMR (DMSO-$d_6$, δ): 1.15–1.95 (5H, m), 2.65–2.85 (1H, m), 2.93–3.13 (1H, m), 3.58–4.10 (2H, m), 4.02 (2H, s), 4.62 (1H, s), 5.21 (1H, br s), 6.55–6.65 (2H, m), 6.94 (1H, dd, J=7.8, 7.8 Hz), 7.15–7.45 (10H, m)

MALDI-MS (m/z): 484 (M+H)⁺

EXAMPLE 21

The following compound was synthesized according to the similar manner to that described for the synthesis of Example 15.

Sodium {[(6SR,7RS)-6-(N,N-diphenylcarbamoyloxy) methyl-7-hydroxy-6,7,8,9-tetrahydro-5H-benzocyclohepten-1-yl]oxy}acetate IR (KBr): 3398, 2922, 1712, 1595, 1493, 1421 cm⁻¹

NMR (DMSO-$d_6$, δ) 1.10–1.55 (2H, m), 1.75–1.98 (1H, m), 2.10–2.67 (3H, m), 3.03–3.45 (2H, m), 3.82–3.98 (1H, m), 4.03 (2H, s), 4.18–4.33 (1H, m), 4.73 (1H, br s), 6.32 (1H, d, J=7.8 Hz), 6.55 (1H, d, J=7.8 Hz), 6.86 (1H, dd, J=7.8, 7.8 Hz), 7.20–7.50 (10H, m)

MALDI-MS (m/z): 484 (M+H)⁺

What is claimed is:

1. A compound of the formula:

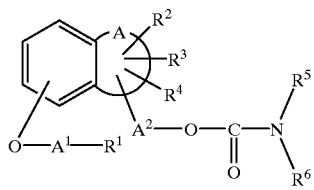

(I)

wherein $R^1$ is a carboxy group or a protected carboxy group, $R^2$ and $R^3$ are each a hydrogen atom, a hydroxy group or a protected hydroxy group, or may be combined together to form an oxo group or a lower alkylene group, $R^4$ is a hydrogen atom, a hydroxy group or a protected hydroxy group, $R^5$ and $R^6$ are each an optionally substituted aryl group, $A^1$ and $A^2$ are each a lower alkylene group, and A and two adjacent carbon atoms of the benzene ring to be bonded with A form a seven-membered ring optionally having an oxygen atom and optionally substituted with an epoxy group and its salt.

2. A compound of claim 1, wherein

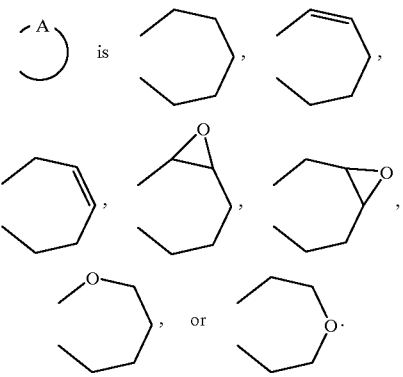

3. A compound of claim 1, wherein $R^1$ is a carboxy group or an esterified carboxy group.

4. A compound of claim 3, wherein $R^2$ is a hydrogen atom or a hydroxy group, $R^3$ is a hydrogen atom or a hydroxy group, and $R^4$ is a hydrogen atom or a hydroxy group.

5. A compound of claim 4, wherein $A^1$ is a methylene group, and $A^2$ is a methylene group.

6. A pharmaceutical composition which comprises, as an active ingredient, a compound of claim 1 or a pharmaceutically acceptable salt thereof in admixture with a pharmaceutically acceptable carrier.

7. A method for treating arterial obstruction, restenosis or ischemic complications after coronary angioplasty, arteriosclerosis, cerebrovascular disease, ischemic heart disease, or dermatosis which comprises administering a compound of claim 1 or pharmaceutically acceptable salt thereof to human or animals.

8. A process for preparing a pharmaceutical composition which comprises admixing a compound of claim 1 or a pharmaceutically acceptable salt thereof with a pharmaceutically acceptable carrier.

* * * * *